(12) United States Patent
Errico

(10) Patent No.: US 8,976,008 B2
(45) Date of Patent: *Mar. 10, 2015

(54) CROSS-DOMAIN COLLABORATIVE SYSTEMS AND METHODS

(75) Inventor: Stephen Errico, Charlotte, NC (US)

(73) Assignee: PrivacyDataSystems, LLC, Charlotte, NC (US)

(*) Notice: Subject to any disclaimer, the term of this patent is extended or adjusted under 35 U.S.C. 154(b) by 412 days.

This patent is subject to a terminal disclaimer.

(21) Appl. No.: 13/553,370

(22) Filed: Jul. 19, 2012

(65) Prior Publication Data

US 2012/0284516 A1    Nov. 8, 2012

Related U.S. Application Data

(63) Continuation-in-part of application No. 12/572,396, filed on Oct. 2, 2009, now Pat. No. 8,266,443, and a continuation-in-part of application No. 12/493,057, filed on Jun. 26, 2009, now Pat. No. 8,527,751, and a (Continued)

(51) Int. Cl.
| | |
|---|---|
| *G05B 19/00* | (2006.01) |
| *H04L 29/06* | (2006.01) |
| *G06F 21/32* | (2013.01) |
| *G06Q 50/22* | (2012.01) |

(52) U.S. Cl.
CPC ............ *H04L 63/0861* (2013.01); *G06F 21/32* (2013.01); *G06Q 50/22* (2013.01); *H04L 63/0442* (2013.01); *H04L 63/168* (2013.01)
USPC .......... 340/5.82; 713/186; 713/190; 382/115; 380/30; 726/26

(58) Field of Classification Search
CPC .... G06F 21/32; G06Q 50/22; H04L 63/0861; H04L 63/0442; H04L 63/168
USPC ......... 340/5.82; 713/168, 165, 170, 171, 186, 713/169, 176, 182; 726/7, 13, 22, 5; 380/255, 44
See application file for complete search history.

(56) References Cited

U.S. PATENT DOCUMENTS

| | | | |
|---|---|---|---|
| 5,541,994 A | * | 7/1996 | Tomko et al. .................. 380/30 |
| 6,078,916 A | | 6/2000 | Culliss |
| 6,202,151 B1 | | 3/2001 | Musgrave et al. |
| 6,594,693 B1 | | 7/2003 | Borwankar |
| 7,043,555 B1 | | 5/2006 | McClain et al. |

(Continued)

*Primary Examiner* — Omer S Khan
(74) *Attorney, Agent, or Firm* — Clements Bernard PLLC; Christopher L. Bernard; Lawrence A. Baratta, Jr.

(57) ABSTRACT

The present disclosure relates to systems and methods for secure and authentic electronic cross domain collaboration between a plurality of users using a combination of biometric security, a separate and secure network infrastructure, management processes, encrypted electronic storage, and collaborative templates. In an exemplary embodiment, an cross domain collaboration system includes a server including a network interface connected to the Internet, a data store including electronic data storage, and a processor, wherein each of the network interface, the data store and the processor are communicatively coupled, and wherein the network interface, the data store and the processor are collectively configured to: biometrically authenticate a plurality of users, wherein each of the plurality of users comprises a security level and a domain; and enable cross domain collaboration between the plurality of users based on the security level of each of the plurality of users.

18 Claims, 27 Drawing Sheets

Related U.S. Application Data continuation-in-part of application No. 11/880,017, filed on Jul. 19, 2007, and a continuation-in-part of application No. 11/509,279, filed on Aug. 24, 2006, now abandoned, and a continuation-in-part of application No. PCT/US2009/040175, filed on Apr. 10, 2009, and a continuation-in-part of application No. PCT/US2009/056183, filed on Sep. 8, 2009.

(60) Provisional application No. 61/095,279, filed on Sep. 8, 2008.

(56) References Cited

U.S. PATENT DOCUMENTS

| | | | |
|---|---|---|---|
| 7,239,346 | B1 | 7/2007 | Priddy |
| 7,711,152 | B1 | 5/2010 | Davida et al. |
| 2002/0007453 | A1 | 1/2002 | Nemovicher |
| 2002/0176583 | A1 | 11/2002 | Buttiker |
| 2002/0199194 | A1 | 12/2002 | Ali |
| 2003/0009698 | A1 | 1/2003 | Lindeman et al. |
| 2003/0044050 | A1 | 3/2003 | Clark et al. |
| 2003/0046237 | A1 | 3/2003 | Uberti |
| 2003/0195935 | A1 | 10/2003 | Leeper |
| 2004/0005051 | A1 | 1/2004 | Wheeler et al. |
| 2004/0010697 | A1 | 1/2004 | White |
| 2004/0054885 | A1 | 3/2004 | Bartram et al. |
| 2004/0250085 | A1* | 12/2004 | Tattan et al. .................. 713/186 |
| 2005/0055306 | A1 | 3/2005 | Miller et al. |
| 2005/0066357 | A1 | 3/2005 | Ryal |
| 2005/0177380 | A1 | 8/2005 | Pritchard et al. |
| 2005/0198170 | A1 | 9/2005 | LeMay et al. |
| 2006/0161761 | A1 | 7/2006 | Schwartz et al. |
| 2007/0005717 | A1 | 1/2007 | LeVasseur et al. |
| 2007/0038704 | A1 | 2/2007 | Brown et al. |
| 2007/0208952 | A1* | 9/2007 | Nation et al. .................. 713/190 |
| 2007/0280510 | A1* | 12/2007 | Owen et al. .................. 382/115 |
| 2008/0150678 | A1 | 6/2008 | Giobbi et al. |
| 2008/0180212 | A1 | 7/2008 | Aikawa et al. |
| 2008/0184374 | A1* | 7/2008 | Mohnl et al. .................... 726/26 |
| 2009/0150968 | A1 | 6/2009 | Ozzie et al. |

* cited by examiner

CLIENT INQUIRY FORM

For correspondence, please complete all fields below to send an ePackage (secure communications) to our company First Name: [          ]  ←902

Last Name: [          ]

Email: [          ]

Confirm Email: [          ]

Phone No.: [          ]

Comments: [          ]

Attachments:  ←904  ←906

File 1: [          ] [Browse]

File 2: [          ] [Browse]

File 3: [          ] [Browse]  ←908

File 4: [          ] [Browse]

File 5: [          ] [Browse]  [SEND]

*FIG. 8*

SEND ePACKAGE

| 1. Message | 2. Recipients | 3. Attach Files | 4. Instances |

Name: John Doe (John.Doe@senditcertified.com)
Send Text Alert? ☐
Electronic Signature: ☐   Access Code: [_____]   Fingerprint: ☐

SEND

*FIG. 15*

DISPLAY

Date:
From:
To:
Subject:
 Message
  Notes:

Shared Documents:

*FIG. 16*

DISPLAY

Date:
From:
To:
Subject:
Message

Notes:

Shared Documents:      Permission
- [ ] Full
- [ ] Reply/Forward
- [ ] View /Read Only
- [ ] Print Allowed
- [ ] Screen Capture Prevent
- [ ] Screen Mask On

*FIG. 25*

CROSS-DOMAIN COLLABORATIVE SYSTEMS AND METHODS

CROSS-REFERENCE TO RELATED APPLICATION(S)

The present patent application is a continuation-in-part of and claims priority to the following U.S. Patent Applications, PCT Patent Applicants, and/or U.S. Provisional Patent Applications, the contents of which are incorporated by reference herein:

| Title | Ser. No. | Filing Date |
|---|---|---|
| SYSTEMS AND METHODS FOR SECURE AND AUTHENTIC ELECTRONIC COLLABORATION | 12/572,396 | Oct. 2, 2009 |
| SYSTEMS AND METHODS FOR SECURE AND CERTIFIED ELECTRONIC MESSAGING | 12/493,057 | Jun. 26, 2009 |
| METHOD TO RECORD AND AUTHENTICATE A PARTICIPANT'S BIOMETRIC IDENTIFICATION OF AN EVENT VIA A NETWORK | 11/880,017 | Jul. 18, 2007 |
| METHOD TO IMPROVE THE INTEGRITY OF INTERNET PROGRAMS, WEBSITES AND SOFTWARE | 11/509,279 | Aug. 24, 2006 |
| IMPROVED CERTIFIED EMAIL MESSAGES AND ATTACHMENTS | PCT/US2009/40175 | Apr. 10, 2009 |
| SECURE MESSAGE AND FILE DELIVERY | PCT/US09/56183 | Sep. 8, 2009 |
| SECURE MESSAGE AND FILE DELIVERY | 61/095,279 | Sep. 8, 2008 |

FIELD OF THE INVENTION

The present invention relates generally to electronic collaboration. More particularly, the present invention relates to cross domain electronic collaboration systems and methods for secure and authentic collaboration between a plurality of users using a combination of biometric security, a separate and secure network infrastructure, management processes, encrypted electronic storage, various security rules, and cross domain collaborative templates.

BACKGROUND OF THE INVENTION

Within government, industry, and the like, cross domain collaboration has always been difficult to manage and implement due to varying security clearances, desire to limit insider knowledge on a need to know basis, and the like. As such, a set of rules and procedures have been developed implementing such collaboration through physical means. Cross domain collaboration may generally be defined as the sharing of information across different companies, organizations, governmental agencies, and the like. Specifically, current methodologies utilize paper-based rules that may include security levels (e.g. classified, top secret, unclassified, etc.) with various content at differing levels and redacting associated content above a user's security level. Unfortunately, this process is labor-intensive and slow as information must be manually sorted and parsed across the various domains.

Online applications are proliferating as the Internet evolves. For instance, various collaborative applications are now widely used enabling large numbers of users from anywhere to work on a project, meeting, and the like. For example, exemplary collaboration types include Microsoft Sharepoint (available from Microsoft Corp.), LiveMeeting (available from Microsoft Corp.), wiki technologies such as wikipedia.org, gotomeeting.com (available from Citrix Online LLC), and the like. This online collaboration allows users to instantly share documents, calendars, notes, video, audio, etc. from anywhere. Advantageously, online collaboration provides productivity improvements, organizational synergy, and the like. Unfortunately, there are problems associated with existing collaboration techniques such as identity verification, security, privacy, proof of delivery, spam, viruses, and other harmful malware. Also, existing collaboration techniques use the "very public and very vulnerable" Internet as their worldwide network. The challenge is how to collaborate with users and determine the legitimacy or know the true intentions of the users in the world of the "Unvetted Public Internet".

With respect to cross domain collaboration, there exists a need to implement the current methodologies effectively and efficiently electronically.

BRIEF SUMMARY OF THE INVENTION

In an exemplary embodiment of the present invention, a cross domain collaboration system includes a server with a network interface connected to the Internet, a data store comprising electronic data storage, and a processor, wherein each of the network interface, the data store and the processor are communicatively coupled, and wherein the network interface, the data store and the processor are collectively configured to: biometrically authenticate a plurality of users, wherein each of the plurality of users comprises a security level and a domain; and enable cross domain collaboration between the plurality of users based on the security level of each of the plurality of users. Each of the plurality of users communicates to the server through a secure connection over the Internet, wherein the secure connection over the Internet comprises a Hypertext Transfer Protocol Secure (HTTPS) connection, and wherein the secure connection traverses outside at least one domain of the plurality of users. The network interface, the data store and the processor are collectively further configured to: enable one of the users to set up the cross domain collaboration and invite participants comprises the plurality of users; and adjust the security level of one or more of the plurality of users, wherein the security level is adjusted downward only. To biometrically authenticate a user of the plurality of users, the network interface, the data store and the processor are collectively configured to send software code to a device associated with the user; scan a fingerprint of the user at the device; create a numerical index of the fingerprint responsive to the scan of the fingerprint to form a public key; receive the public key from the device; and authenticate the public key with a corresponding private key in an authentication database. The network interface, the data store and the processor are collectively further configured to: register the user for biometric authentication, wherein to register comprises capturing a fingerprint scan of the user and storing a private key in the authentication database responsive to the fingerprint scan; and set the security level of the user. The cross domain collaboration comprises a sharing of files comprising any of text, video, audio, file attachments, calendars, contact lists, memos, to do lists, schedules, action item lists, announcements, and task lists between the plurality of users. The files are stored in the data store and encrypted with one of Triple Data Encryption Standard (T-DES) and Advanced Encryption Standard (AES) encryption. The data store comprises a plurality of templates for the cross domain collaboration. The network interface, the data store and the processor are collectively further configured to: create a new template and store the created template among the plurality of templates; and adjust security associated with one of the plurality of templates. The network interface, the data store and the processor are collectively further configured to: tag all information posted to the cross domain collaboration with a certain security level; and restrict viewing of the information among the plurality of users based on the certain security level associated with the information. The network interface, the data store and the processor are collectively further configured to: code word classify information in the cross domain collaboration responsive to an analysis of the information.

In another exemplary embodiment, a cross domain collaboration method includes receiving a selection of a template from a plurality of templates for a cross domain collaboration; adjusting security associated with the selected template; receiving a list of a plurality of users for the cross domain collaboration; adjusting security associated with each of the plurality of users; biometrically authenticating each of the plurality of users prior to participation in the cross domain collaboration; and displaying information in the cross domain collaboration based on a security level of each user. The cross domain collaboration method further includes creating a custom template for the cross domain collaboration. The template comprises a collection of any of text, video, audio, file attachments, calendars, contact lists, memos, to do lists, schedules, action item lists, announcements, and task lists. Biometrically authenticating includes sending software code to a device associated with a user of the plurality of users; scanning a fingerprint of the user at the device; creating a numerical index of the fingerprint responsive to the scan of the fingerprint to form a public key; receiving the public key from the device; and authenticating the public key with a corresponding private key in an authentication database. The cross domain collaboration method further includes registering the user for biometric authentication, wherein to register comprises capturing a fingerprint scan of the user and storing a private key in the authentication database responsive to the fingerprint scan; and setting security for the user. The cross domain collaboration method further includes communicating with each of the plurality of users through a secure connection over the Internet for the cross domain collaboration. The secure connection over the Internet comprises a Hypertext Transfer Protocol Secure (HTTPS) connection. Files associated with the cross domain collaboration are stored in a secure data store and encrypted with one of Triple Data Encryption Standard (T-DES) and Advanced Encryption Standard (AES) encryption.

In yet another exemplary embodiment, a secure computer system connected to a plurality of users includes a cross domain server with a network connection to the Internet; an authentication database communicatively coupled to the hosted server; a data store communicatively coupled to the cross domain server, wherein the data store comprises data storage for a cross domain collaboration; a plurality of users each with a networked device connected to the Internet, wherein the networked device comprises a biometric authentication device and each of the plurality of users comprises a security level; wherein the cross domain server is configured to host the cross domain collaboration between the plurality of users through a secure Hypertext Transfer Protocol Secure (HTTPS) connection to each of the plurality of users and through biometric authentication of each of the plurality of users prior to accessing the online collaboration, and wherein information is displayed to each of the plurality of users based upon a security level associated with each of the plurality of users.

BRIEF DESCRIPTION OF THE DRAWINGS

The present invention is illustrated and described herein with reference to the various drawings, in which like reference numbers denote like method steps and/or system components, respectively, and in which:

FIG. 8 is a webpage illustrating a user interface (UI) sending a certified ePackage according to an exemplary embodiment of the present invention;

FIGS. 13-16 are screenshots of displays related to online collaboration and ePackages according to exemplary embodiments of the present invention;

FIG. 25 is a screen shot of viewing management for files in an exemplary ePackage.

DETAILED DESCRIPTION OF THE INVENTION

In various exemplary embodiments, the present invention relates to cross domain electronic collaboration systems and methods for secure and authentic collaboration between a plurality of users using a combination of biometric security, a separate and secure network infrastructure, management processes, encrypted electronic storage, various security rules, and cross domain collaborative templates. Advantageously, the present invention utilizes a hosted or cloud-based solution for a plurality of users to interact with one another view various file types and real-time communications in a secure and verified manner.

Figure 1:
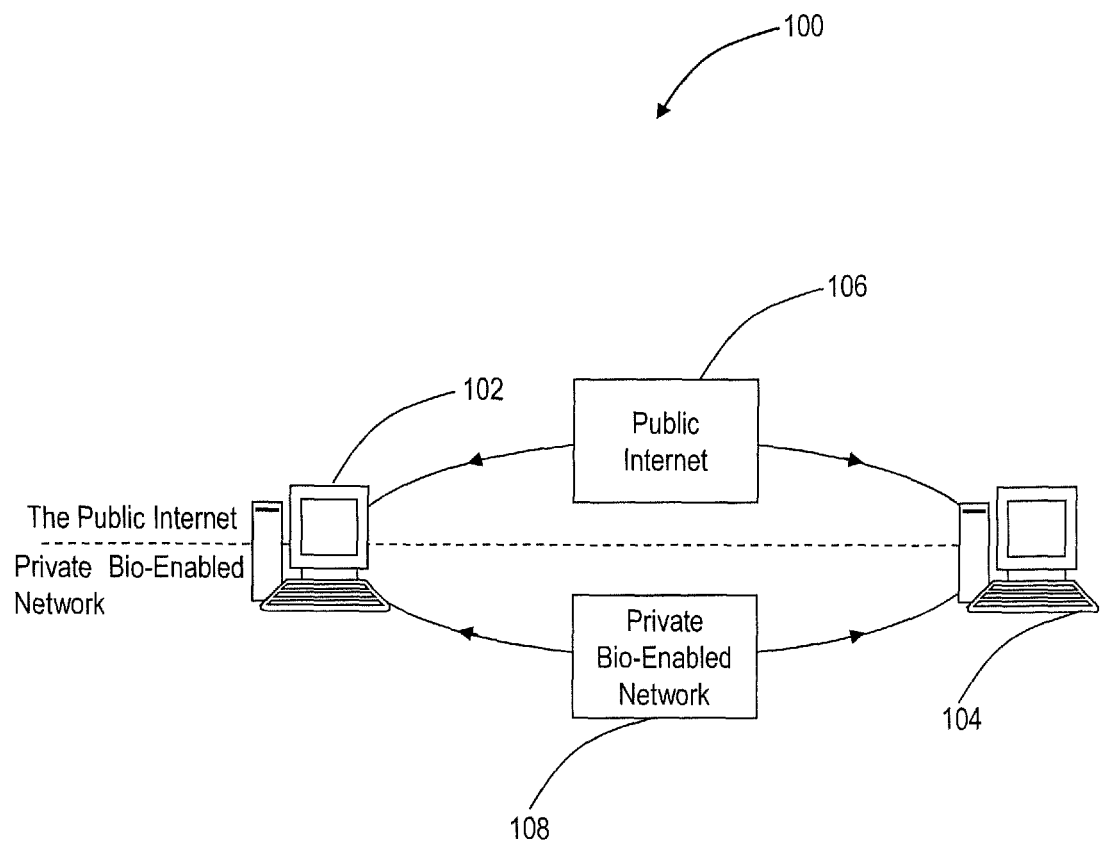
FIG. 1 is a high-level network diagram of a message exchange between two users interacting in the Public Internet versus a Private, Bio-Enable Network according to an exemplary embodiment of the present invention.

Referring to FIG. 1, a high-level network diagram 100 illustrates a message exchange of two users 102, 104 interacting in the Public Internet 106 versus a Private, Bio-Enable Network 108 according to an exemplary embodiment of the present invention. In this diagram 100, the users 102, 104 represent a person, organization, etc. with the ability to send electronic messages over the Internet 106. Electronic messages can include electronic mail ("email"), file exchange such as through email attachments or file transfer protocol (FTP), audio-visual messaging, instant messaging, text messaging, and the like. Disadvantageously, conventional message exchanges over the Public Internet 106 includes minimal security, unvetted senders/recipients, lack of bio-identify verification, limited proof of delivery, limited encryption, limited large file support, substantial virus/malware exposure, endless spam, and the like.

The present invention provides a biometric-enabled, point-to-point encrypted, certified electronic messaging system over the Private, Bio-Enable Network 108 providing a worldwide community of users with the highest levels of identity verification, security and privacy, and proof of delivery when exchanging important, high-value email messages and files. Messages can be in text, audio and visual formats, with large attachments (e.g., up to four gigabytes in size, but larger sizes are also contemplated). Recipients can either read the sender's email text message, hear the sender speak the message, or watch (and hear) them speak. Advantageously, the present invention provides certified email or other electronic messaging senders and recipients with the highest levels of Biometric Identify Verification, Security and Privacy, and Proof of Delivery. Additionally, the present invention supports various message formats as well. By utilizing state-of-the-art biometrics (initially registered fingerprint scans), the ultimate in identify verification; which confidently answers the question, "Is that really you?" Various levels of vetting are provided via Credit Card authorization, fingerprint scan, Notary Public certification, phone number, address, email address, and the like. By utilizing its own private, fully-encrypted, network and infrastructure for exchanging personal messages, i.e. the Private, Bio-Enable Network 108, the present invention avoids the privacy and security problems that come with many everyday, public email systems and their use of the low-security and vulnerable public Internet 106.

The present invention provides enhanced Proof of Delivery by utilizing its email management processes for email composition and logging (recording) all related delivery events as they occur, such as: when the sender's certified email was sent, when an alert notification (eDelivery email form, SMS, IVR, . . . ) was sent to their recipient(s), if and when the certified email was "signed for" (and how they signed—e.g., by fingerprint scan or electronic signature, this is called "delivery acceptance"), and if and when an attachment was viewed and/or downloaded. The present invention also can utilize three sender options for creating a message itself, 1) text (words), 2) audio (voice message) and 3) visual (video with sound). Again, recipients can either read the sender's email text message, hear the sender speak the message, or watch and hear them speak it. This multi-option set of formats is not the simple attaching of text (the written word), audio (voice) or visual (video) files to an email message. These message options relate to integration with, and are specific to, the main purpose of the email message itself, and are not "just attachments" to an email. The addition of audio and visual format options to the standard text format option provides senders more effectiveness, more preciseness, more personalization and more flexibility (e.g., no keyboard use necessary) in creating their communications with the intended recipient.

The inventors have an initial preferred embodiment of a company, a website, a network, an infrastructure, a series of servers, an email management system and an operator to support the implementation of a certified email system with the main processes described below. Such website, network, infrastructure, servers and email management system is collectively the first-ever, biometric-enabled, point-to-point encrypted, certified email system providing a worldwide community of users with a "complete solution" including the highest levels of identity verification, security and privacy, proof of delivery and effectiveness in communications when exchanging important, confidential, high-value email messages and attachments. These email messages can be communicated in text, audio and visual formats, and include large attachments, for example 4 gigabytes or larger in size.

It's important to point out that there are usually two email systems used with the Invention. First, there is the registered user's current, everyday email system (e.g., Hotmail, AOL, MSN, Outlook, etc.), if they have one, where they will receive alerts (called eDelivery forms) from the Invention that say "you've got certified mail". Note—such alert notices can also be sent to a user's cell phone (via SMS—Short Message System) or to their land line phone (via IVR—Integrated Voice Response), or equivalent, if such alert options are selected by the user. Second, there is the Invention's separate, private, high-security email network and infrastructure (including secure servers) that such users utilize when actually sending, receiving, tracking and managing email messages and attachments via the Invention's website (referred to as "website" or "system" or "the Invention's website or system" in the process discussion below). Just as the Post Office, FedEx and UPS uses completely different processes and infrastructures for their certified mail/package delivery services, the Invention uses a similar separation concept in its management and transport of certified email messages and attachments.

Figure 2:
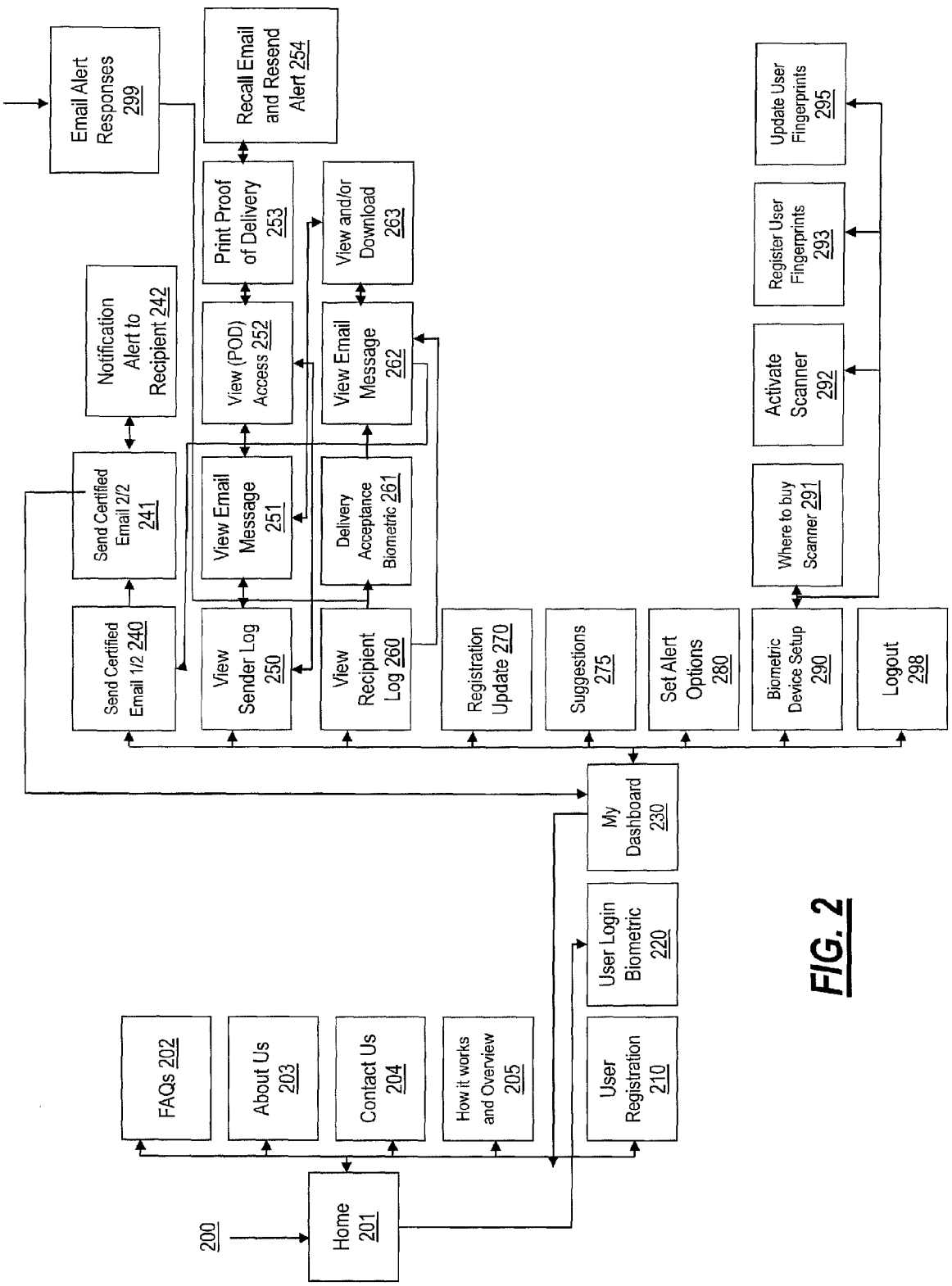
FIG. 2 is a flowchart of various processes associated with creating, sending, and managing certified electronic messages according to an exemplary embodiment of the present invention.

Referring to FIG. 2, a flowchart illustrates various processes 200 associated with creating, sending, and managing certified electronic messages according to an exemplary embodiment of the present invention. These processes 200 are executed on one or more computers or servers connected to a network, such as the Internet. Collectively, the processes 200 enable a user to send a certified electronic message to another user. A Home process 201, as illustrated in FIG. 2, is the starting point for users of the present invention. Note that processes 201 through 299 are all illustrated in FIG. 2. The Home process 201, allows users to become more informed as to the present inventions' features, functions and purpose through access to Frequently Asked Questions (FAQ's) 202, About Us 203, Contact Us 204 and How It Works 205.

To become a user of the present invention, a visitor selects a User Registration process 210 to fill out required user information, including (for example) an existing email address they want to use as their User ID when logging into the website, and a password. This process allows users to register to officially use the Invention and is designed to do initial vetting of the users. Other information gathered can include: name, address, phone number, and credit card number; to insure the operator has a good understanding of who is using the Invention. Other user information is gathered in other processes, for example, a user's fingerprint and a Notary Public certification. They can also receive a registration confirmation notice at the email address they supplied (or by SMS or IVR, if such option is selected by user) and they will have to respond in order to activate their user status and be able to login to the website going forward. If they do not receive an email confirmation notice, they should be sure that their spam filter has not intercepted it for some reason; that happens occasionally when using the email notice option.

The present invention's certified email messages and attachments are private and confidential between sender and recipient, and its registered users are vetted in many ways (credit card, fingerprint, notary certification, phone number, address, email address and more). And, such vetting levels are displayed by the system to both senders and recipients. The system does not allow mass marketing companies, who send large numbers of emails to recipients (that they may or may not know), to become registered users of the website. These companies and spammers in general have no ability to send large numbers of emails in the Invention; which has purposely limited the number recipients per email to dissuade any such attempt by any registered user. The present invention works on the premise that vetted user/senders (identified at various levels) are far less likely to intentionally send a virus, spyware or other malware in their emails and attachments. A registered user's current, everyday email address is often used as their User ID in the Invention's website. Their cell phone number or landline phone number can also be used as a User ID in the system as well as a user-selected ID. These are also a key in its databases and can only be changed by special system request.

Registration and usage of the website or system can require paying a monthly or annual fee; or, a per-unit (per email) fee can be charged. There are many ways to charge for such services. Registered users of the Invention can initially have service levels as follows (which are subject to change): 1) unlimited sending and receiving of local and international emails via the system, each with a 4 GB attachment maximum, 2) 10-20 GB in long-term attachment storage and 3) 100 GB in monthly download bandwidth. Additional storage and bandwidth can be purchased.

To get started after a new user's status is activated, the user selects a User Login process 220 to sign in and start a user session. After login, the user automatically proceeds to a "My Dashboard" process 230 (further described below). This requires the User ID and password to be provided during the registration process. Once the user installs an approved fingerprint scanner and registers their actual fingerprint with the system (and optionally confirms it with a separate Notary Public certification), which activates the biometric features of the system, then users can scan their fingerprint in lieu of entering the password. As a bio-registered user that uses their fingerprint scanner to login, a recipient sees that the sender is at one of the highest levels of vetting in the system and their emails are identified as being "biometrically certified".

To send or compose a certified message or mail, the user selects "Send (Compose) Certified Mail" processes 240, 241 to compose certified email messages and send each to a set number of recipients at a time. After initially registering, it is suggested that a new user send the system a certified "Hello" email. The user can send one to themselves as well to experience the recipient "delivery acceptance" process and add an "Access Code" (a secret code only they and their recipients know) to make it even more secure. The access code is pre-determined between sender and recipient and can be used in combination with an electronic signature, a fingerprint, or both. When users select the "Send (Compose) Certified Mail" processes 240, 241 and begin with the process 240 then proceed to the process 241 to create their certified email and identify the recipients. There are a variety of reasons for this two-step compose process, including the need to determine if the specified recipients are already registers users (and if they have their fingerprint registered as well); which would give the sender more options to specify their recipients' delivery acceptance rules. They can enter a text version of the email "subject line" and "message" (other formats described below) at this point and identify all intended recipients. If such an alert option is selected in a process for setting alerts, the email subject line is also displayed in the alert notice (eDelivery form), generated in process 242, sent to the recipient to inform them that have certified email waiting for delivery. The subject line gives them an idea of what the email concerns.

Because the system informs the user/sender if they have entered an email address for a registered or unregistered recipient, as they proceed from processes 240 to 241, senders can then set the delivery acceptance rules for each recipient and select their attachments in process 241. These delivery acceptance rules can include 1) an electronic signature (the default), 2) an access code (a secret code or password only known by the sender and the recipient), 3) a fingerprint scan to insure the recipient's identity (note—the system knows if a recipient has activated this biometric capability), and 4) the sender can insist that a non-registered recipient registers before taking delivery of their certified email. For non-registered recipients the sender is required to spell their name (first and last) for the system so the electronic signature process knows what name to check for during delivery acceptance.

Audio and visual email message format options, also created on the "Compose Certified Email" process, are described below. Email Message Format Options—the "Send (Compose) Certified Email" process 240 supports three options (text, audio and visual) for the email message formats that users can select (plus any number of attachments in process 241). This adds flexibility and precision to a user's email message exchanges, as previously explained herein. So, after recipients "take delivery" of a sender's email, they can read the words written by the sender, hear the sender speak their words or see and hear them speak their words. The numerous combinations of text, audio and visual formats, presented in an integrated and coordinated fashion within the Invention's certified email system, create an appealing and powerful way to send email messages, including: 1) a text message by itself, 2) text message and attachment, 3) audio message, 4) audio message and attachment, 5) visual message, and 6) visual message and attachment. The combinations are many and ultimately get to this combination: a text message, an audio message, a visual message and an attachment (one or many).

In the "Attachment" process (a sub process within Send-Compose Email Message process 241), the Invention's system allows for the attachments in many formats such as PDF, DOC, pictures, voice files, movie files, virtually any of the formats can become attachments within the system's secure environment. In this system, the user is essentially uploading their attachments to the Invention's secure server rather then attempting to send them to, and risk clogging up of, the recipient's everyday email system. This is particularly a problem with very large files causing many such emails to be rejected (a.k.a. "Undelivered Mail Returned to Sender"). When a recipient receives (i.e., takes delivery of) the system's certified email message (in process 261) they also can take delivery of the attachments (in process 263 via process 262), if supplied by the sender. The sender can also designate whether the attachment can to be "viewed" only or if the recipient cam also be allowed to actually download it (see process 263). If view only, the file does not physically leave the invention's secure servers and, as a result, is not transferred to the recipient's computer. Each of these actions is logged, as they occur, to provide the sender proof of delivery and proof of what files were delivered and how.

Alert Notifications, i.e. "You've got certified email" alert notices, are sent in a Notification Alert to Recipient process 242 to all recipients based on the alert options set by the user in "Set Alert Options" process 280. Alert notices can be sent (potentially multiple times, to insure prompt pick up) via email, cell phone (using SMS) or landline phone (using IVR). Alerts sent via email can include (if such option is selected by user) a Uniform Resource Locator (URL) link back to the Invention's website where the user can gain access to the certified email and its attachments. But, first they must go through a Delivery Acceptance process 261. If such option is selected by the user in the process 280, alerts can also be sent to users of the system to indicate that activity has occurred on certified emails and attachments they have previously sent. This could include, for example, that a recipient has taken delivery of (e.g., signed for delivery) of the email the user sent them. This saves the user from having to log into the system to determine that this has occurred. For textual, audio and visual email messages sent by users in the Send (Compose) Certified Email processes 240, 241, such certified messages can also be delivered directly to a cell phone (or cell phone-computer device like the Apple iPhone) or landline phone via IVR as long as the recipient can prove who they are and can meet the delivery requirements (e.g., identity verification) set by the sender in process 241.

Users can select a "View Sender Log" process 250 or a "View Recipient Log" process 260 to monitor the sending and delivery process for certified emails. Remember, when users send a certified email via the website, an alert notice is also sent to their recipient's email address in the process 242 which contains a "you've got certified mail" notice and a URL link back to the system's separate, high-security infrastructure where they can "sign for" and "take delivery" of the sender's private email message in the Delivery Acceptance process 261 (e.g., electronically sign for delivery, similar to the FedEx or UPS process when they come to a recipient's front door) and any attachments the sender may have also sent. After delivery acceptance, users can view, hear or see the certified email message in a View Email Message process 262 and access related attachments in View and/or Download Attachments process 263.

The sender and recipient logs (the processes 250, 260) in the Invention provide valuable tracking information. They tell the sender (and recipient) when the user's certified email was sent, when an alert notice email was sent to the recipient(s), if and when the certified email was "signed for" (called "delivery acceptance" process 261), and if and when it was viewed and/or downloaded. Note—if a user is logged in (process 220) to the website and receives an email from another registered user of the system (or from themselves when testing the Invention), they can take delivery (process 261) of the email from within the website directly from the Recipient Log process 260, just as if they had clicked the link provided on the alert notice email from the sender, if so selected by user in the Set Alert Options process 280. Note—such alert notices can also be sent via cell phone using SMS or landline phone using IVR, or equivalent, if so selected in the process 280.

From the View Sender Log process 250 senders can "recall" or "resend" (in process 254) their previously sent certified email messages and attachments, sent via the Invention. This gives the sender the ability to quickly react if they made a mistake or if the recipient wanted the alert notice sent to a different address or in a different format. In other, everyday email systems, there is no certainty that a sender can successfully recall (pull back) an email before it is placed for viewing in the recipient's email system (especially if there are multiple recipients). This Invention does allow the sender to recall the certified email and be certain, by viewing the related sender log entries (in processes 250, 252), that a specific recipient (which could be one of many) has or has not yet seen the contents.

Print Log and Proof of Delivery Document—Users can print a "Proof of Delivery" (a.k.a. "Proof of Service") document in process 253 by going to the View Sender Log process (250) and selecting a specific email that was previously sent and then selecting "Access". This access log receipt process 252 displays the Email and Attachment Access Log with all the delivery activity events (listed above) on this certified email to date. Select the "Print POD Log" process 253 to print the "Proof of Delivery" document which shows the original certified email contents and lists attachment(s). It also lists all recipients and the delivery acceptance requirements that were set by the sender. Also, a log of events will be displayed that shows all relevant delivery activity for the selected email. Proof of Delivery emails and CD's (or other media) can also be available to allow the actual attached files and voice and visual/video files be made available to those want to prove the circumstances related to such certified emails and attachments sent via the Invention. This Proof of Delivery can potentially be used for various purposes, such as, for example, legal service and the like.

Fingerprint Scanners are utilized in the present invention, i.e. refer to the Biometric Device Setup process 290 for general information on all such devices and their activation. The Invention's system supports fingerprint scanners in its biometric identity verification processes and can be purchased via the website's operators or elsewhere on the Internet. Refer to Where to Buy Fingerprint Scanner process 291 for specific information on where and how to buy such a device. The Invention can support a U.are.U 4000B USB Reader from DigitalPersona, Inc. of Redwood City, Calif., and may support other vendors' devices in the future. The system also supports other models of DigitalPersona's biometric product line, including those that are built into many popular computer laptops like those from Dell and Lenovo (previously IBM). If not a "built-in" as just mentioned, the system's users have to buy specific, approved fingerprint scanner devices from the Invention's operators or as directed in process 291 because such devices may have to utilize drivers modified to support the Invention's unique, browser-based biometric implementation and operational processes. If users already own a 4000B USB reader, they may need to contact the system's operator for special instructions on installation (refer to process 290). Note—until users have an approved scanner, ignore (bypass) the fingerprint process on the Login process 220. In the interim, registered users can use (for example) their email address and private password to complete login. Once a biometric identity capability is implemented, this option to use a password may or may no be approved, based on several variables and user set options.

A user can select a "Registration Update" process 270 to make basic changes in user information. Some user information cannot be changed on this screen and, as a result, users have to contact the operator to help with that change (e.g., email address as the user's User ID). This is necessary because this has become a "key" field in a database and must be changed in a special process. Notice that the website can be optionally gathering the user's cell phone number as well because the system can be sending text alerts messages (in the Notification Alert to Recipient process 242) to cell phones (and to land line phones, as telephone companies implement this and equivalent features in the future), based on user options set in the Set Alert Options process 280.

A user can select the Biometric Device Setup process 290 to setup and activate biometric devices supported by the Invention. Fingerprint scanner software drivers can be downloaded and the device activated in an Activate Fingerprint Scanner process 292 to support the installation on the user's computer. And, a user's actual fingerprints can be initially "registered" in a Register User Fingerprint(s) process 293 and subsequently updated (changed) in an Update User Fingerprint process 294. This means the user's fingerprint is scanned and a numeric representation is stored for use in the Invention's matching and identification algorithms. As other devices are added to the Invention's biometric capabilities, the process 290 can be expanded. Note—the system does not store the actual fingerprint image for any of its registered users; rather a numeric representation.

The "My Dashboard" process 230 provides a view of the registered user's personalized Dashboard which provides a high-level, control window for the user's many global communications activities in the system. The Dashboard is where users land (go to) after each Login process 220 and after the Send (Compose) Certified Email processes 240, 241 and both View Log processes 250, 260. The Invention uses a window on this screen to inform all registered users with various news and update items. The Invention can also provide a ticker tape (rolling) window here to display and monitor, as they occur, the delivery activity events of many certified emails simultaneously, and provide other insightful real-time statistics about the user's entire experience with the Invention. Lastly, select a "Suggestions" process 275 to let the websites operators know of user suggestions and problems, as they occur. The Invention provides FAQ's 202 that are very helpful in answering user questions. A Log Out process 298 is used to log out and terminate the current user session of the Invention's website.

In an exemplary embodiment, a method of communication between a sender and a recipient initiates once a sender logs onto "SenditCertified.com", a private network, and identifies themselves. The sender composes a message via text, audio and/or video format on a network device. A network device is a computer, a cellular phone, a PDA, or other type device capable of communicating with a server or computer. The sender then seals the message via a biometric identification, secret access code, electronic signature or by independent verification. In other words the sender seals the message by identifying himself or herself, preferably by biometric identification. Thereafter the server of the private network encrypts the message and the sender sends it to the recipient over the private network. The private network does not use the Internet, does not use server to server duplication or store and forward protocol. The encrypted message proceeds from the sender's network device to the private network server where it waits delivery to the recipient. The server notifies the recipient of the message and states the conditions under which the recipient can take delivery of the message. After the recipient meets the conditions to take delivery, the server un-encrypts the message and the recipient takes delivery of the message, via a second network device, which may be under the control of the recipient.

The server tracks the progress of the send message, records the tracking information, such as time and place sent, size of message, type of message, conditions of delivery, and recipient identification, such as name, secret access code, biometric identification information and/or other information of recipient. The biometric identification may be fingerprinting, iris scan, facial recognition, or DNA. Preferably the biometric information is fingerprinting. Additionally, the sender and recipient may confirm their identity via an independent vetting process with said private network. The independent vetting process may include electronic signature, secret access code, or other independent information, such as credit card numbers, answering secret questions, driver's license, and/or passport or social security information.

Figure 3:
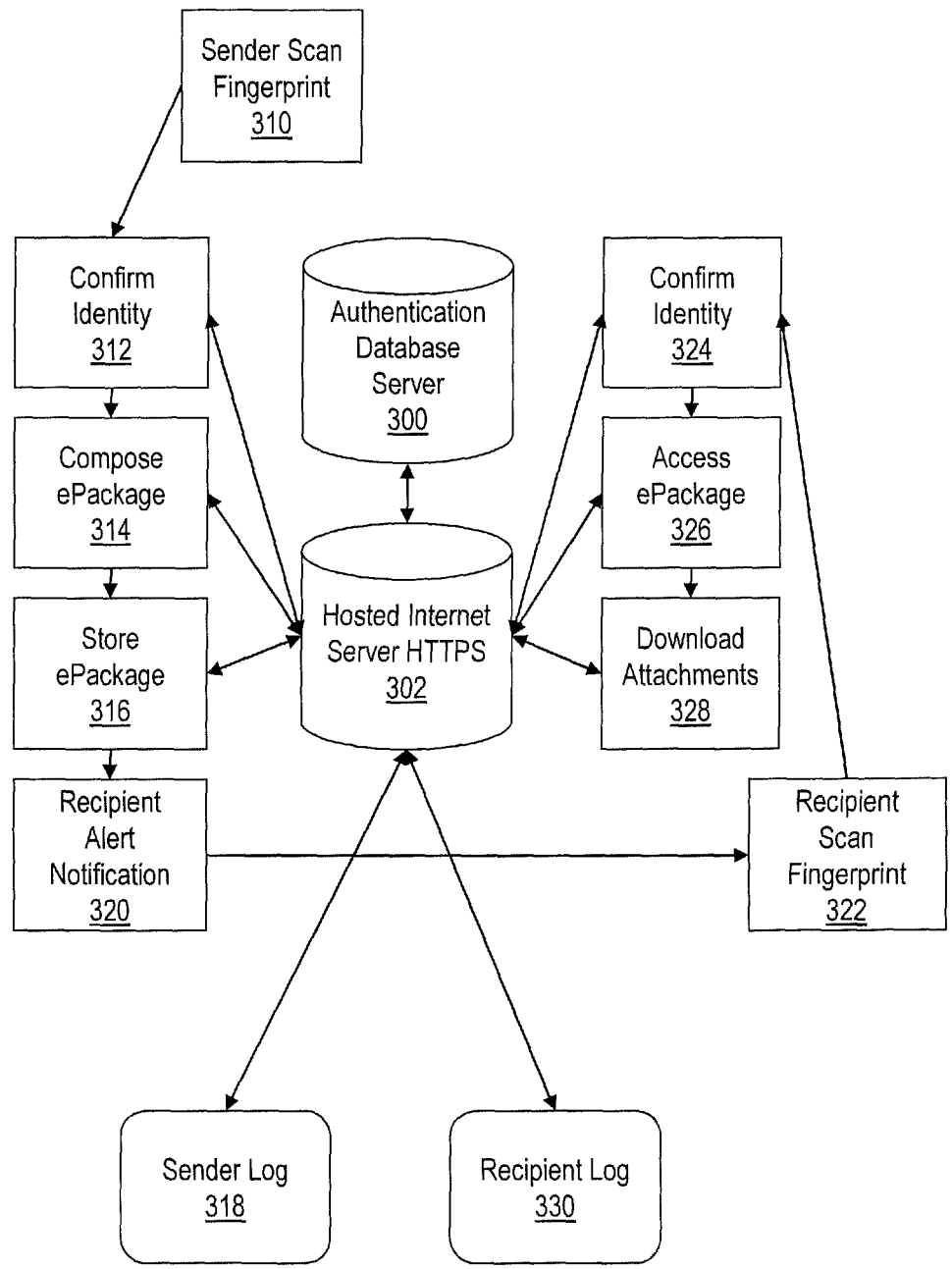
FIG. 3 is a flowchart of various processes interacting with an Authentication Database Server and a Hosted Internet Server for providing secure, certified electronic messaging according to an exemplary embodiment of the present invention.

Referring to FIG. 3, a flowchart illustrates various processes interacting with an Authentication Database Server 300 and a Hosted Internet Server 302 for providing secure, certified electronic messaging according to an exemplary embodiment of the present invention. As described herein, the secure, certified electronic message can be referred to as an "ePackage" that is a combination of pre-organized communication components (e.g., a package containing a text, a voice and/or video message, and attached files). An ePackage may have large file attachments, e.g., four gigabytes in size. With messages in text, audio, and video formats, ePackage recipients may either read the senders' textual messages, hear the senders speak the messages, or watch (and hear) them.

The present invention is built as a private network over the Internet, e.g., using secure connections over the Internet, rather than as an add-on to prior email protocols. The various process functions described herein can be executed on the Hosted Internet Server 302, and users interact with the Hosted Internet Server 302 via a web browser and, as a result, ePackages never leave the control of the Hosted Internet Server 302. Interactive capabilities are accomplished using Active Server Pages (ASP) code and HyperText Markup Language (HTML) for screen rendering. Alternative embodiments may use PHP, Net, Java, or other Internet environments. Data for user sessions are stored using a database management system, for example, Structured Query Language (SQL) server.

When a registered user logs into the Hosted Internet Server 302 to send an ePackage, a Hypertext Transfer Protocol Secure (HTTPS) connection is established between the user's computer, and the Hosted Internet Server 302. This layer of security can be enhanced by certified encryption, e.g. VeriSign or GeoTrust certifications. Here, the present invention can use Transport Layer Security (TLS) and its predecessor, Secure Sockets Layer (SSL), as cryptographic protocols that provide security and data integrity for communications over networks such as the Internet. TLS and SSL encrypt the segments of network connections at the Transport Layer end-to-end. The secure connection includes a secure web address and the user interacts with the Hosted Internet Server 302 via a browser, e.g. Internet Explorer, Firefox, Netscape, Safari, and the like. The system prompts the user, via a browser to enter login data, a part of which is the user's fingerprint. Alternatively, the system may accept a password from a user, but then the system marks messages for the session with a lesser authentication level.

In step 310, the Hosted Internet Server 302 can request a fingerprint scan of the user by displaying a fingerprint icon. A link to the Hosted Internet Server 302 can be pending waiting for the fingerprint scan. When a finger of a user who desires to log in and send a message is scanned, the Hosted Internet Server 302 receives a fingerprint image or numerical representation of the fingerprint from the user. The fingerprint scan can be accomplished via an off-the-shelf biometric scanner. In some embodiments, the fingerprint scanner is a USB device, such as the U.are.U 4000B USB Reader from Digjtalpersona, Inc., attached to a personal computer. In other embodiments, the scanner is built into a person computer, such as an Upek built into a Dell laptop. In prior systems, the results from scanners would go into a PC or a LAN. In the present invention, the results of the scan are transmitted to a web-based, Hosted Internet Server 302 via a browser interface. Thus, the system is available for use worldwide.

The fingerprint scan results in an image of the user's fingerprint. The process can convert the image scanned to an index (i.e., a long numeric number) that uniquely identifies the finger. In some embodiments, the conversion is done with a hash index and public and private key encryption. In step 312, the process generally uses a standard "public key/private key" technique to safeguard a user password. Accordingly, the index created from the users fingerprint is encrypted as further described below regarding step 406 of FIG. 4. The present invention uses a three tier procedure to accomplish authentication. Tier 1: The local computer reads the scan and creates a numeric key (public key). Tier 2: The public key is transmitted to the Hosted Internet Server 302. Tier 3: The Hosted Internet Server 302 transmits a request to the Authentication Database Server 300, and the public key must correctly match the private key to get authentication. This very secure process, if identity is authenticated, allows the registered user further access to the system.

After successful identity authentication, the user is inside a secure area of the process and can access multiple functions. The user can choose next to compose an ePackage. As shown in step 314, the user composes an ePackage. The user enters (creates or assembles) the components of the ePackage via a web-based graphical user interface (GUI). In step 316, the process stores the ePackage components into an SQL database on the Hosted Internet Server 302. The process then allows the user/sender to perform other tasks, e.g. review a log of previously sent ePackages provided by the process in step 318. The process may also receive a logoff indication from the user.

After the user submits the ePackage, in step 320, the process sends an alert notification to the recipients) chosen by the sender during the ePackage composition step. Each recipient receives an alert as indicated by the sender. The alerts may be in the form of, e.g. an email alert, a cell phone text messaging alert, a voice alert, or a combination thereof based on the senders choice and the capabilities of the recipient. The recipient may either log in to the system as a user or the recipient could click on an alert link to the system that was sent to them in step 318. The alert link may show the recipient only the sender's name and contact information and the sender's identity authentication level so that the recipient can make an informed decision about taking delivery of the actual ePackage.

In step 322, the process allows an ePackage recipient to access the system. The step is analogous to step 310 used to allow senders access to the system. When the recipient logs in or clicks the alert link they are now able to take delivery of the ePackage, but must first be authenticated in accordance with the identity verification requirements requested by the sender. The sender may have requested an electronic signature, an access code, a fingerprint scan, another identifier, or a combination thereof. The system will then authenticate the recipient to make sure they meet the requested identity authentication level. If a fingerprint is requested, in step 322, the process displays a fingerprint icon and a link to the server will be pending and waiting for the recipient's scan. In step 324, the process then authenticates the identity of a recipient in a manner essentially similar to that used in step 312 to authenticate the identity of a sender.

After successful recipient authentication, in step 326, the system presents the ePackage for access via the user's browser, and the user may read the message text, listen to the sender's voice recording by simply clicking a speaker icon, or view the sender's video by clicking a video icon. In step 328, the user may then choose to view or download the attachments that the sender may have included. If the recipient is a registered user, they may then perform other system tasks or simply logoff.

During each of the steps in the biometric ePackage process, the process writes an event log record into the SQL database. In step 318, the process provides senders with real-time status/tracking information of their ePackages via the sender log. The process may optionally send an activity notification to the sender, for example, by text message alert, when the sender's ePackage was received/accessed/downloaded by the intended recipient. In step 318, the process provides senders with detailed logs of what activities each recipient has taken. Senders log in to the system via steps 310 and 312 to access this information. These logs may be printed or electronically sent to provide evidence of proof of delivery and proof of the content of messages and files in an ePackage. In step 330, the process provides ePackage recipients with status/tracking information analogous to that provided senders in step 318. Recipients must be registered users to view their recipient logs, to see their previous ePackages, and to access proof of delivery.

Figure 4:
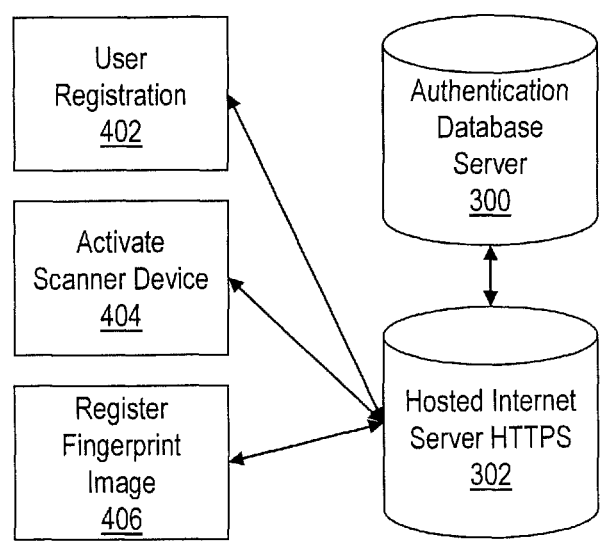
FIG. 4 is a flowchart of various processes interacting with the Authentication Database Server and the Hosted Internet Server for providing biometric authentication according to an exemplary embodiment of the present invention.

Referring to FIG. 4 a flowchart illustrates various processes interacting with the Authentication Database Server 300 and the Hosted Internet Server 302 for providing biometric authentication according to an exemplary embodiment of the present invention. For the process to allow a user to access the Hosted Internet Server 302 with a high level of identity authentication, the process must have previously registered both a scanner device and the user's fingerprint image. The process registers users to access the system in step 402. When a user of the system initially registers, it includes specifying a password. When a user is ready to enhance their service from password-level verification to fingerprint scan authentication, they access a "my account area" of the system. In the "my account area," the process creates and updates user information, such as, email address, phone numbers, and mailing address. In step 404, the process activates one or more fingerprint scanners for the previously registered user. The scanner may be a built in model or a USB model that can be attached to a computer. The process activates the scanner by running a program on the local computer. The program checks for compatibility of the local computer and the scanner. Compatibility may include information such as the computer manufacturer and driver type for the fingerprint reader. The program acquires this information by, for example, reading machine register device records. The installation program may install any missing software components along with scanner client software.

After successful completion of step 404, the system can use the activated scanner device with the user's account. The system allows scanners to be physically interchangeable, but the computer must have the proper drivers for its scanner type. After scanner activation, in step 406, the process registers a fingerprint image of the user. In this step, the user's fingerprint scanner is started, the user is requested to select a finger and make multiple scans. Repeated scans help ensure that the process creates a good repeatable public and private key for matching algorithms. The private key is then stored on the Authentication Database Server 300 and the public key is stored in the user record on the Hosted Internet Server 302. The user is now registered to access the system and to send and receive ePackages with identity authenticated by fingerprint.

Although fingerprints are the form of biometric identification described herein, other biometric identifiers are also contemplated by the present invention. For example, other biometric identifiers can include iris scans, facial scans, retinal scans, or DNA indicia. These biometric identifiers may be used individually or in combination. Additionally, a combination of biometric identifiers may be used along with smart cards or other devices that may be carried by a user. For example, peripheral devices can be included to provide fingerprint capture. Additionally, peripheral devices can provide retinal scans as well.

Figure 5:
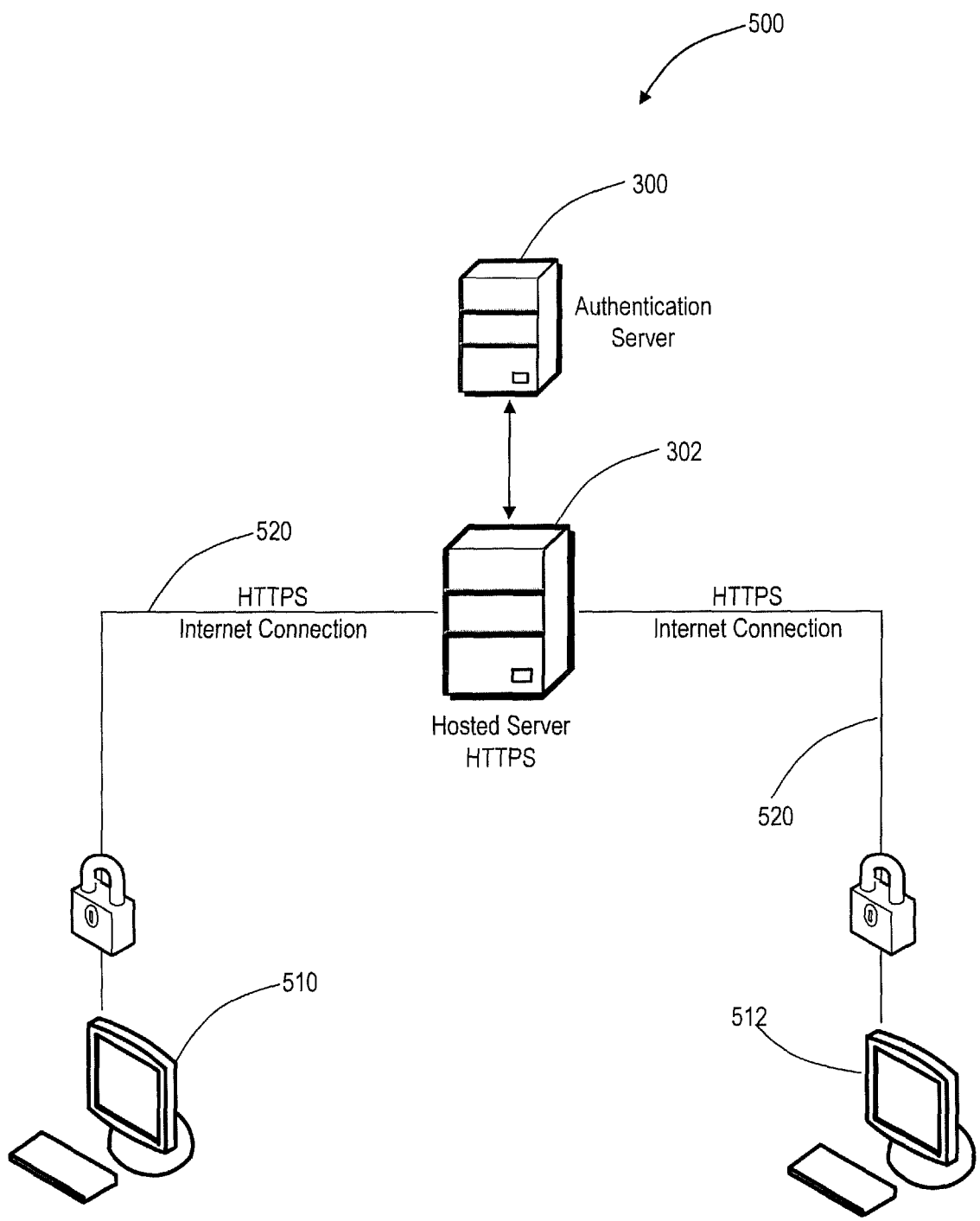
FIG. 5 is a diagram of a network illustrating secure, certified electronic exchange according to exemplary embodiments of the present invention.

Referring to FIG. 5, a diagram of a network 500 illustrates secure, certified electronic exchange according to exemplary embodiments of the present invention. FIG. 5 illustrates the network 500 showing secure message exchange between users 510, 512, i.e. a message exchange between two users. The present invention contemplates other scenarios as well such as a message exchange between a plurality of users to one or more users.

In the present invention, all users (message senders and recipients) communicate with the Hosted Internet Server 302 utilizing Hypertext Transfer Protocol Secure (HTTPS) connections 520 over the Internet or other types of secure connections. This differs from conventional electronic message exchange where email messages are sent between the users' mail servers. The ePackages are created and sent/received to/from the Hosted Internet Server 302 through HTTPS 520 connections and thus are always secure. HTTPS is a combination of the Hypertext Transfer Protocol (HTTP) and a cryptographic protocol (e.g. a true 512-bit SSL). Existing web browsers (i.e., Internet Explorer, Firefox, Netscape, Safari, Chrome, Opera and the like) are configured with integrated HTTPS support, i.e. the users 510, 512, 516, 518 can directly access the Hosted Internet Server 302 over HTTPS with their web browsers. Accordingly, the present invention provides transmission, storage, path and identity verification.

The HTTPS 520 connections encrypt a session with a digital certificate i.e., HTTP over SSL (Secure Sockets Layer) which can be used by Web browsers and HTTPS-capable client programs. A secure website first sends a user's browser a public encryption key, which is used to construct another, unique, non-public encryption key. This key, which is known only to the web server and the user, is then used to protect all subsequent transfers of information. In practice, SSL provides a secure tunnel between two points on the Internet. Files transferred along this tunnel are wrapped in a layer of encryption that makes them impossible for third parties to view or compromise. Using this SSL solution, the present invention can ensure complete data confidentiality. The encryption methods used are based on keys only available to the user and the Hosted Internet Server 302, making it virtually impossible to decode the data sent, even if it is intercepted. This SSL solution also ensures data integrity—no outside source can modify data as it travels between an end user and the Hosted Internet Server 302. If data is changed in transit, the protocol automatically recognizes the modification and asks the client to resubmit the file.

The network 500 illustrates an example where the user 510 sends an ePackage to the user 512. Here, the user 510 logs into the Server 302 over the HTTPS connection 520 and composes text, audio, video, and/or attachments that are stored on the Server 302. The user 512 is notified as specified by the user 510 and the user 512 logs into the Server 302 over the HTTPS connection 520 to view and/or download the ePackage.

As shown in FIG. 5, the present invention does not utilize the traditional "store and forward" method of electronic messaging, which can leave copies of emails on multiple servers around the Internet. The present invention encrypts ePackage contents, sends them over a private pathway of the Internet to the Hosted Internet Server 302 and never interacts with another email system. The recipient then downloads the encrypted message through another private pathway to their own computer. All ePackages can be encrypted with T-DES or with the Advanced Encryption Standard (AES). Additionally, this encryption can prevent network operators of the Hosted Internet Server 302 from viewing the contents of stored ePackages.

From a physical perspective, the servers 300, 302 may be located at the same or separate location and the users 510, 512 may be connected to the servers 300, 302 through any type of Internet connection (wireless, DSL, cable modem, T1, T3, etc.). In an exemplary embodiment, the servers 300, 302 are located in a SAS 70 Type II Certified Data Center with security, redundant power, redundant HVAC (heating, ventilation, air conditioning), etc. Further, the data center may include network security protection that prevents denial-of-service (DOS) attacks and uses traffic profiling and anomaly detection capabilities, to manage and secure connections from the servers 300, 302 to the Internet, to pinpoint and troubleshoot network attacks, to monitor our servers and applications, and to analyze network security performance issues. The servers 300, 302 may communicate to one another via an internal, secure storage area network (SAN).

Additionally, the data center may configure the servers 300, 302 with a hardened operating system (OS). Specifically, this may include disabling of unnecessary services on the servers 300, 302, renaming the administrator account to a less common name, disabling of decoy and guest accounts and preventing remote access to accounts, disabling of anonymous FTP to the servers 300, 302, enhanced logging on the servers 300, 302, registry changes on the servers 300, 302 to add security to various parameters, and the like.

Figure 6:
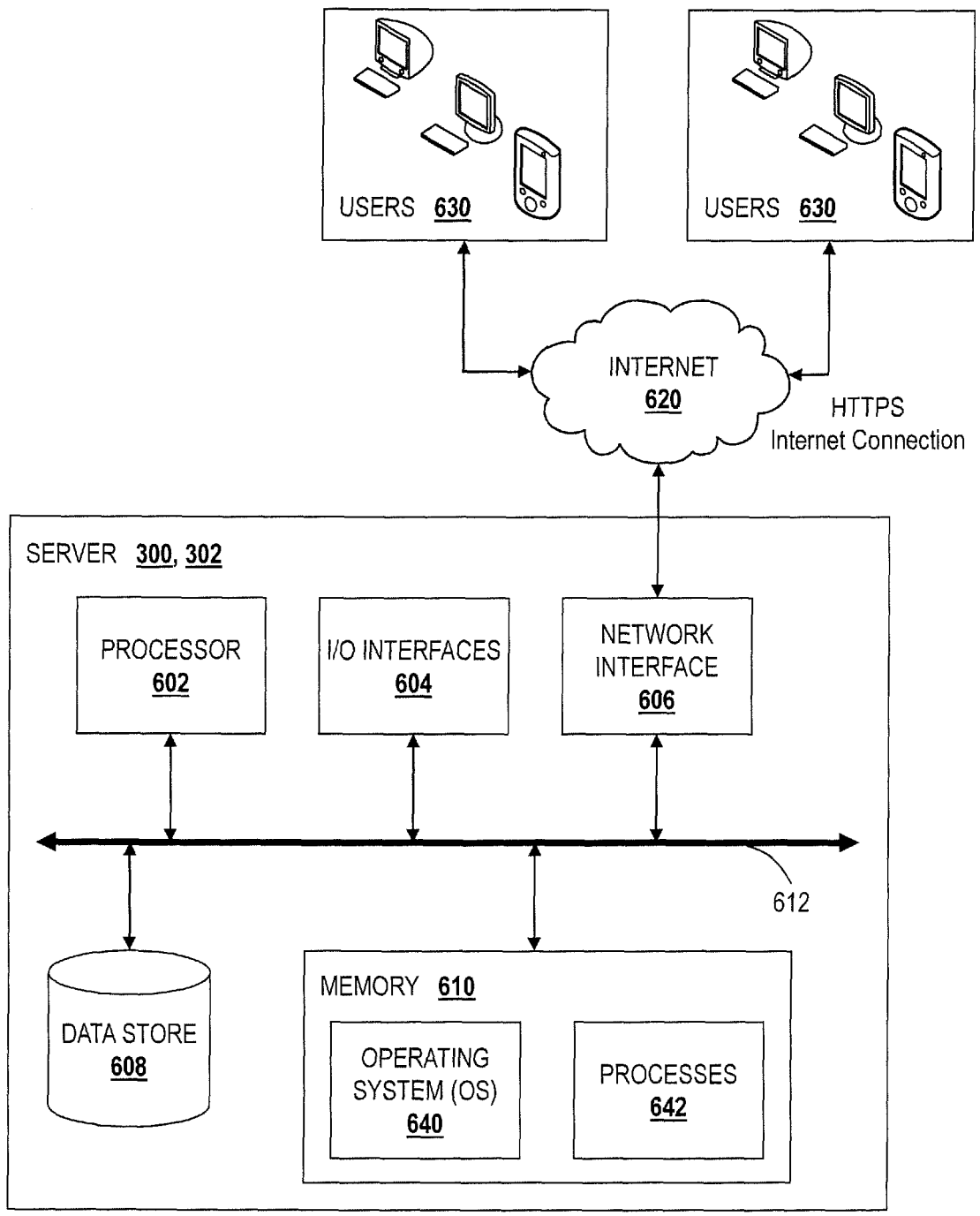
FIG. 6 is a diagram of various components of the Authentication Database Server and the Hosted Internet Server according to an exemplary embodiment of the present invention.

Referring to FIG. 6, a diagram illustrates various components of the Authentication Database Server 300 and the Hosted Internet Server 302 according to an exemplary embodiment of the present invention. The servers 300, 302 can be a digital computer that, in terms of hardware architecture, generally includes a processor 602, input/output (I/O) interfaces 604, network interfaces 606, a data store 608, and memory 610. The components (602, 604, 606, 608, 610) are communicatively coupled via a local interface 612. The local interface 612 can be, for example but not limited to, one or more buses or other wired or wireless connections, as is known in the art. The local interface 612 can have additional elements, which are omitted for simplicity, such as controllers, buffers (caches), drivers, repeaters, and receivers, among many others, to enable communications. Further, the local interface 612 can include address, control, and/or data connections to enable appropriate communications among the aforementioned components.

The processor 602 is a hardware device for executing software instructions. The processor 602 can be any custom made or commercially available processor, a central processing unit (CPU), an auxiliary processor among several processors associated with the server 300, 302, a semiconductor-based microprocessor (in the form of a microchip or chip set), or generally any device for executing software instructions. When the server 300, 302 is in operation, the processor 602 is configured to execute software stored within the memory 610, to communicate data to and from the memory 610, and to generally control operations of the server 300, 302 pursuant to the software instructions.

The I/O interfaces 604 can be used to receive user input from and/or for providing system output to one or more devices or components. User input can be provided via, for example, a keyboard and/or a mouse. System output can be provided via a display device and a printer (not shown). I/O interfaces 604 can include, for example, a serial port, a parallel port, a small computer system interface (SCSI), an infrared (IR) interface, a radio frequency (RF) interface, and/or a universal serial bus (USB) interface.

The network interfaces 606 can be used to enable the server 300, 302 to communicate on a network, such as the Internet 620. For example, the server 300, 302 can utilize the network interface 20 to communicate to multiple users 630 using HTTPS over the Internet 620. The users 630 can include desktop computers connected to the Internet 620 via a high-speed connection (DSL, Cable modem, WiMax, Cellular, etc.), laptop computers connected to the Internet 620 via the high-speed connection, mobile devices connected to the Internet 620 via a mobile network, and the like. Each user 630 can also include a network interface to communicate to the server 300, 302 to access the various processes described herein. The network interfaces 606 can include, for example, an Ethernet card (e.g., 10 BaseT, Fast Ethernet, Gigabit Ethernet) or a wireless local area network (WLAN) card (e.g., 802.11a/b/g). The network interfaces 606 can include address, control, and/or data connections to enable appropriate communications on the network.

A data store 608 can be used to store data, such as various ePackages from the users 630 and the tracking data in the sender and recipient logs associated with each ePackage. The data store 608 can include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 608 can incorporate electronic, magnetic, optical, and/or other types of storage media. In one example, the data store 608 can be located internal to the server 300, 302 such as, for example, an internal hard drive connected to the local interface 612 in the server 300, 302. Additionally in another embodiment, the data store 608 can be located external to the server 300, 302 such as, for example, an external hard drive connected to the I/O interfaces 604 (e.g., SCSI or USB connection). In yet another embodiment, the data store 608 can be connected to the server 300, 302 through a network, such as, for example, a network attached file server.

The memory 610 can include any of volatile memory elements (e.g., random access memory (RAM, such as DRAM, SRAM, SDRAM, etc.)), nonvolatile memory elements (e.g., ROM, hard drive, tape, CDROM, etc.), and combinations thereof. Moreover, the memory 610 may incorporate electronic, magnetic, optical, and/or other types of storage media. Note that the memory 610 can have a distributed architecture, where various components are situated remotely from one another, but can be accessed by the processor 602. The software in memory 610 can include one or more software programs, each of which includes an ordered listing of executable instructions for implementing logical functions. The software in the memory 610 includes a suitable operating system (O/S) 640 and various processes 642. The operating system 640 essentially controls the execution of other computer programs, such as the various processes 642, and provides scheduling, input-output control, file and data management, memory management, and communication control and related services. The operating system 640 can be any of Windows NT, Windows 2000, Windows XP, Windows Vista (all available from Microsoft, Corp. of Redmond, Wash.), Solaris (available from Sun Microsystems, Inc. of Palo Alto, Calif.), LINUX (or another UNIX variant) (available from Red Hat of Raleigh, N.C.), or the like.

The various processes 642 include the various processes described herein with respect to the Authentication Database Server 300 and the Hosted Internet Server 302 enabling the exchange of secure and certified electronic messages. In an exemplary embodiment, the Authentication Database Server 300 and the Hosted Internet Server 302 can be on separate systems. In another exemplary embodiment, the Authentication Database Server 300 and the Hosted Internet Server 302 can reside in the same system.

Figure 7A:
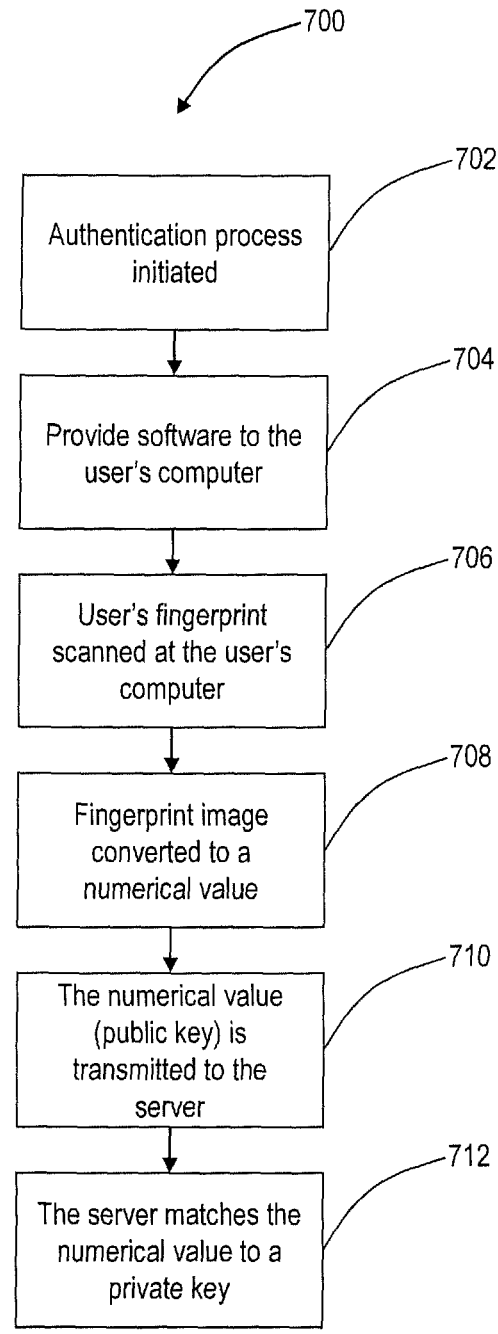
FIGS. 7a-7c are flowcharts and diagrams of an authentication and registration process for authenticating a user via a fingerprint over the Internet according to an exemplary embodiment of the present invention.

Referring to FIG. 7a, a flowchart illustrates an authentication process 700 for authenticating a user via a fingerprint over the Internet according to an exemplary embodiment of the present invention. The process 700 operates on a user's computer equipped with a fingerprint scanning device and a server connected to the user's computer over the Internet. Advantageously, the process 700 enables remote authentication of a user over the Internet. The authentication process 700 is initiated (step 702). The authentication process 700 initiates when there is a need to remotely authenticate a user through the server biometrically. Software is provided to the user's computer from the server over the Internet (step 704). Here, the server provides software to functionally control the remote capture of the user's fingerprint. This can include ASP code, PHP, .Net, Java, or other Internet environments. The software can be provided using VeriSign Code Signing Digital IDs that provide a digital signature to software and macros including Microsoft Authenticode, Microsoft Office and VBA Signing, Sun Java Signing, Adobe Air, Netscape Object Signing, Macromedia Shockwave, and Marimba Castanet Channel Digital IDs for secure delivery over the Internet. Digital IDs are virtual "shrinkwrap" for your software; if your code is tampered with in any way after it is signed, the digital signature will break and alert customers that the code is not trustworthy.

Once loaded, the software prompts the user to provide a fingerprint scan, and the user's fingerprint is scanned at the user's computer through a scanned connected to the computer (step 706). The fingerprint scan results in an image of the user's fingerprint. This image is converted to a numerical value (i.e., a long numeric number) that uniquely identifies the user (step 708). In some embodiments, the conversion is done with a hash index and public and private key encryption. This numerical value is similar to a bar code in a retail store. Also, the process 700 does not keep or transmit the fingerprint image. Further, it is not possible to reconstruct a fingerprint image from the numerical value. The numerical value is transmitted over the Internet to the server (step 710). This numerical value acts as a public key that is transmitted over the Internet to the server (operating as a host server). Once the server receives this numerical value (public key), the server provides this numerical value to an authentication database of private keys (step 712). If the numerical value matches, then the user is authenticated.

Figure 7B:
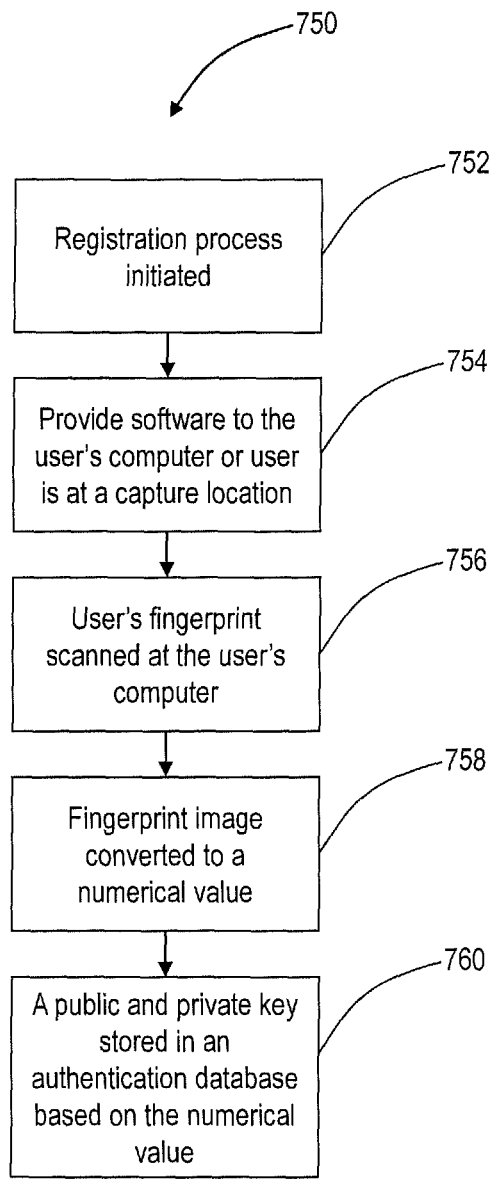

Referring to FIG. 7b, a flowchart illustrates a registration process 750 for registering a user's fingerprint Internet according to an exemplary embodiment of the present invention. The process 750 can operates on a user's computer equipped with a fingerprint scanning device and a server connected to the user's computer over the Internet. Alternatively, the process 750 can operate on a computer and scanner at a central location where the user can be physically identified prior to fingerprint capture thereby providing absolute proof the user is who they say they are. Advantageously, the process 750 can be utilized with the process 700 to enable remote authentication of a user over the Internet. The registration process 750 is initiated (step 752). The registration process 750 can be done either locally at a user's computer or at a central location where the user is physically present to provide their fingerprint capture (step 754). If the registration process 750 is done locally, software is provided to the user's computer from a central server. This software can be downloaded and automatically installed, e.g. a Java application. Alternatively, the user can go to a central location where someone can physically identify the user, e.g. through state-issued ID, birth certificate, etc., and this central location can include a computer with the software. The software interacts with a fingerprint scanner communicatively coupled to the computer.

Once loaded, the software prompts the user to provide a fingerprint scan, and the user's fingerprint is scanned at the user's computer through a scanned connected to the computer (step 756). The fingerprint scan results in an image of the user's fingerprint. This image is converted to a numerical value (i.e., a long numeric number) that uniquely identifies the user (step 758). In some embodiments, the conversion is done with a hash index and public and private key encryption. A public and private key is stored in an authentication database based on the numerical value (step 760). For example, the numerical value can correspond to a public key that will be used in the future to transmit an authentication request to match it to a private key stored in the authentication database.

Figure 7C:
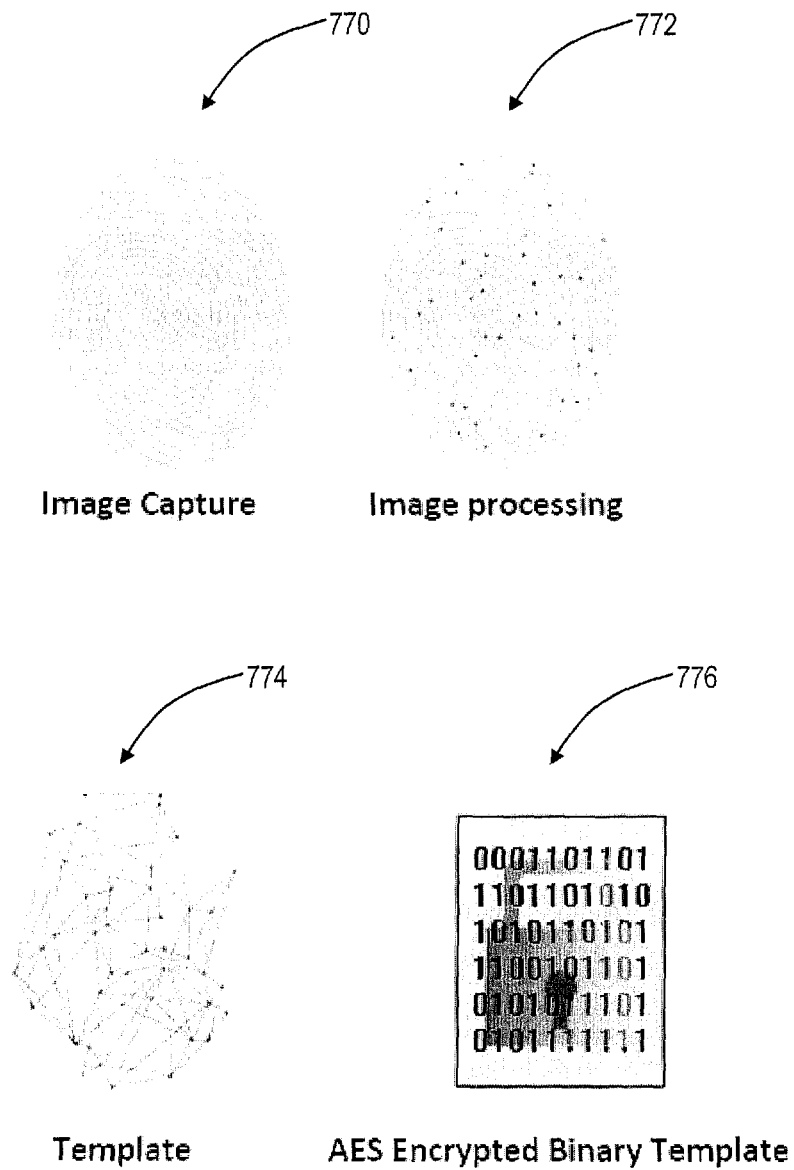

Referring to FIG. 7c, in an exemplary embodiment, diagrams 770, 772, 774, 776 illustrate an exemplary operation of the authentication process 700 from FIG. 7a. These diagrams 770, 772, 774, 776 illustrate the steps 706-710 in the authentication process 700. First, an image capture is performed as shown in the diagram 770. This image capture may be performed by a fingerprint scanner or the like connected to the user's computer. At this point, the user's computer has software that is configured to perform image processing as shown in the diagram 772 to identify reference points in the fingerprint. These reference points are interconnected to form a template as shown in the diagram 774 which is in turn AES encrypted as a binary template as shown in the diagram 776 and transmitted. That is, the numerical value associated with the fingerprint while itself secure, is also transmitted via encryption.

Referring to FIG. 8, a webpage 900 illustrates a UI for sending a certified ePackage according to an exemplary embodiment of the present invention. The exemplary webpage 900 allows any web user to send a message along with secure attachments directly to the webpage 900 owner or the like using the secure messaging mechanisms of the present invention. The webpage 900 is a document or resource of information that is suitable for the World Wide Web (WWW) and can be accessed through a web browser and displayed on a computer screen. This information is usually in HTML or XHTML format, and may provide navigation to other web pages via hypertext links. The webpage 900 is hosted by a host server that connects to the Internet. The webpage 900 includes contact fields 902 for the web user to fill in their name, email (with confirmation), phone number, and any text for comments with the message. An attachment list 904 allows the web user to add multiple files by clicking on a browse button 906 which enables the web user to select a file for attachment (e.g., this can bring up a file or directory list to select the applicable file). The attachment list 904 is illustrated with five attachments, but the number can include more, e.g. ten, or an option to add another attachment to allow any arbitrary number of attachments to be added. Finally, once the message is complete, the web user can select send 908 to complete transmission of the secure ePackage.

The present invention contemplates use with healthcare organizations, government applications, financial services, and other strategic services to provide the utmost security and certification with the exchange of electronic messages. For healthcare, the ePackage provides Health Insurance Portability and Accountability Act (HIPAA) compliance allowing doctors, patients, insurers, and the like to communicate medical records electronically. Also, the ePackage provides compliance to the various security requirements in U.S. law, such as the Sarbanes Oxley (SOX), Gramm-Leach-Bliley Act (GLBA), The Personal Information Protection and Electronic Documents Act, FTC Red Flag, etc. Of note, the present invention requires no hardware and/or software investment on behalf of any organization utilizing the various processes described herein. The Authentication Database Server 300 and the Hosted Internet Server 302 operate over standard HTTPS connections already integrated in conventional web browsers.

Advantageously, the present invention shields sensitive data from hackers, identity thieves, phishing, spamming and unwanted disclosure. File size which is typically limited in email systems is not an issue. The present invention provides an easy method to comply with various security mandates and regulations without infrastructure investment. The proof of delivery processes provides protection from claims of non-delivery and disputes over content along with options for indisputable identity verification using biometric (fingerprint) authentication. Such indisputable identity verification is even superior to conventional paper delivery methods. Thus, the present invention provides complete control of sensitive documents using distribution and storage and a solution to the risks of intercompany communications (i.e., external business exchanges worldwide).

Figure 9:
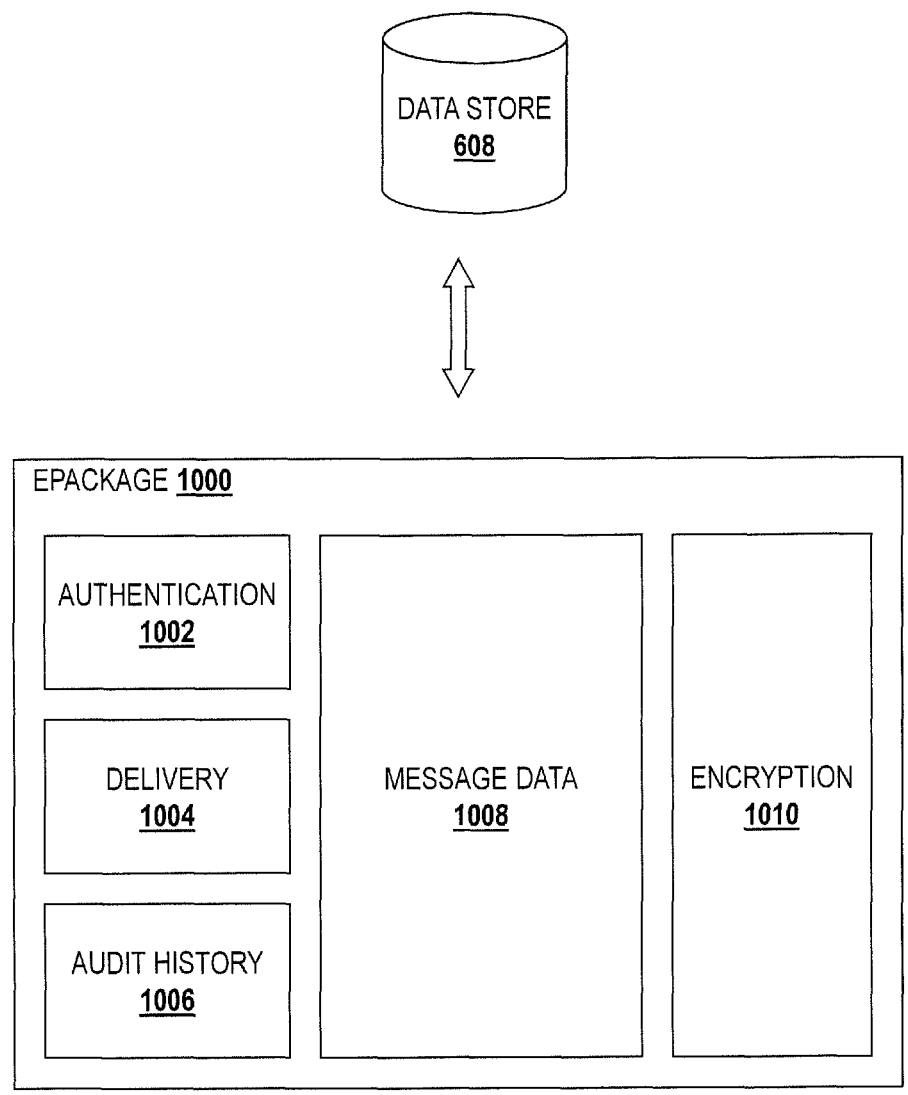
FIG. 9 is an ePackage data structure for a secure and certified electronic messaging according to an exemplary embodiment of the present invention.

Referring to FIG. 9, an ePackage 1000 data structure is illustrated for a secure and certified electronic messaging according to an exemplary embodiment of the present invention. As described herein, the ePackage 1000 is a secure and certified message that is exchanged between users through secure connections to a server (e.g., the Authentication Database Server 300 and the Hosted Internet Server 302). Accordingly, the ePackage 1000 is not forwarded through various routers, switches, mail servers, etc. over the public Internet, but rather a point-to-point delivery from sender to the server and from the server to the receiver all of which is done over a secure, encrypted connection between the sender, receiver, and the server. The ePackage 1000 can be stored in the data store 608 or equivalent. The ePackage 1000 includes authentication information 1002, delivery information 1004, an audit history 1006, message data 1008, and encryption 1010.

The authentication information 1002 can be defined by the sender of the ePackage 1000, and this information 1002 determines how the receiver is certified or verified. Specifically, the sender of the ePackage 1000 can determine various levels of authentication including: none, simply login identification, password-protected, PIN protected, biometric (fingerprint, voice scan, facial scan, retinal scan, etc.), DNA, and the like. Additionally, the sender can select multiple levels for further security and certification, i.e. two or more levels. The delivery information 1004 includes contact information for the sender and the receiver. Additionally, this information 1004 can include how the receiver is notified of the ePackage 1000, e.g. through email, instant messaging, text message, IVR, and the like. The audit history 1006 includes information related to the history of the ePackage 1000, e.g. when created, viewed, downloaded, deleted, etc. This history 1006 is updated each time there is an interaction with the ePackage 1000. The audit history 1006 provides further certification and security of the ePackage 1000 for the sender.

The message data 1008 includes the information being sent from the sender to the receiver. This data 1008 can include text, audio, video, file attachments, and the like. The encryption 1010 provides security and inaccessibility to the ePackage 1008 by anyone not authorized. Specifically, the encryption 1010 can include AES, T-DES, or the like. Also, the encryption 1010 can provide different encryption for different components of the ePackage 1000. Specifically, the message data 1008 can include encryption 1010 that is only accessible by the sender and the receiver. This would prevent the server from viewing the message data 1008. The other information 1002, 1004, 1006 can include encryption that is only accessible by the sender, the receiver, and the server.

Figure 10:
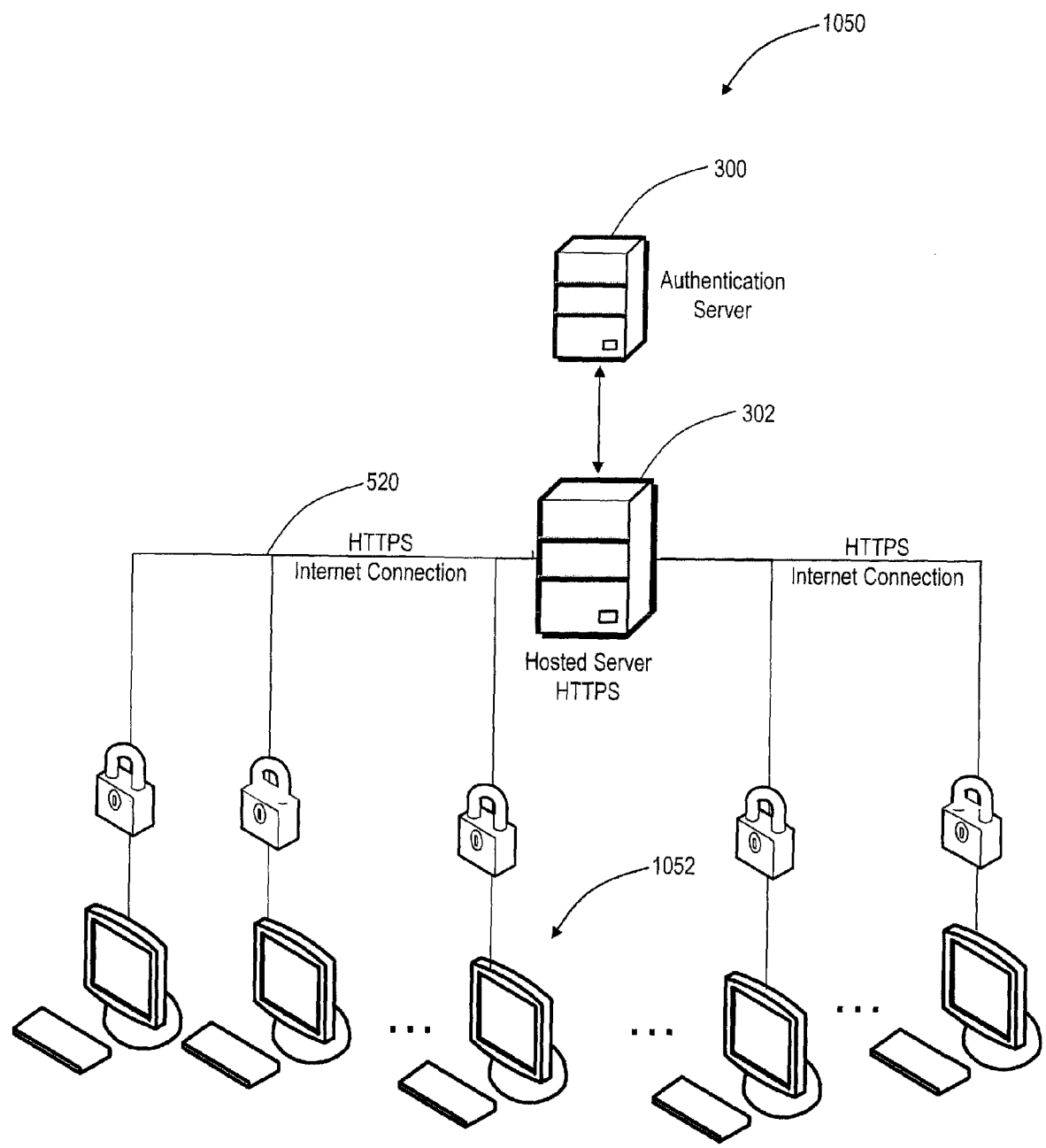
FIG. 10 is a diagram of online collaboration between a plurality of users according to an exemplary embodiment of the present invention.

Referring to FIG. 10, a diagram illustrates online collaboration 1050 between a plurality of users 1052 according to an exemplary embodiment of the present invention. The systems and methods described herein for secure, authentic, certified electronic transmissions can be extended to support online collaborations in a similar fashion. Specifically, the hosted server 302 can be configured to support online collaborations through secure connections 520 to the plurality of users 1052. Further, the online collaboration 1050 can be integrated as one of the processes 200 in FIG. 2, e.g. as another function under the dashboard 230. Advantageously, the online collaboration 1050 provides a website, a network, an infrastructure, a series of servers, an email management system and an operator to support the implementation of a certified and secure online collaboration system.

In general, each of the users 1052 is invited to join the online collaboration through a secure ePackage or the collaboration itself is part on an ePackage. Specifically, the hosted server 302 includes an infrastructure to support collaboration with the users 1052. Each of the users 1052 is biometrically authenticated using the processes described herein. Further, each of the users 1052 work on the online collaboration 1050 through the secure connection 520. Thus, the online collaboration is both secure and all users are authenticated at levels higher than a simple user ID and login. The hosted server 302 is configured to authenticate each of the users 1052 through the authentication database 300. The users 1052 log into the hosted server 302 through the secure connection 520, and can access and modify various components associated with the online collaboration 1050.

Figure 11:
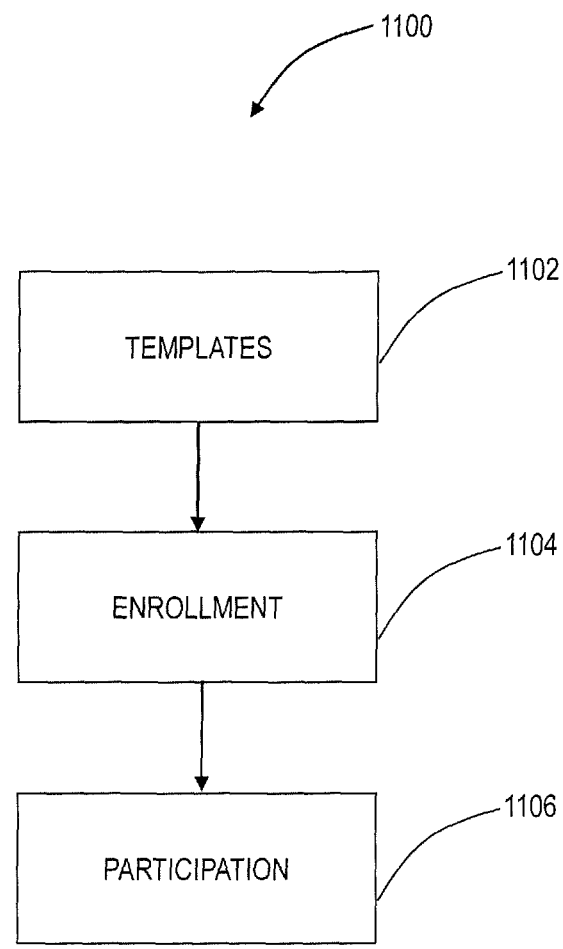
FIG. 11 is a flowchart of online collaboration components for an online collaboration process according to an exemplary embodiment of the present invention.

Referring to FIG. 11, a flowchart illustrates online collaboration components for an online collaboration process 1100 according to an exemplary embodiment of the present invention. Specifically, the online collaboration process 1100 includes templates 1102, enrollment 1104, and participation 1106 phases. The templates 1102 are pre-defined or customized data sets that define a specific type of collaboration. The online collaboration process 1100 includes a plurality of templates 1102 to allow users 1052 to quickly set up a new collaboration. The templates 1102 are akin to a database structure whereby they include fields for text, video, audio, file attachments, calendars, contact lists, memos, to do lists, schedules, action item lists, announcements, task lists, shared documents, and the like. The specific type of template 1102 determines which fields are included. Exemplary template 1102 types can include request for proposals (RFPs), incident reports, new product introduction, medical, and the like. The present invention contemplates the ability for any user 1052 to create a new customized collaborative template 1102 as needed. The process 1100 of online collaboration starts with selection of a pre-defined template or with creation of a new template.

Once the template is defined or selected, the process 1100 requires enrollment 1104 of all of the users involved in the online collaboration. The online collaboration is started by one or more users selecting the template. First, these one or more users are authenticated and confirmed such as through biometric authentication. Now that the online collaboration has started, these one or more users can select the participants in the online collaboration, i.e. for enrollment. This can be accomplished through sending an ePackage to each of the participants. Other methods are also contemplated such as email, text message, instant message, voice mail, etc. Once each of the participants is notified, they each must enroll in the online collaboration such as through biometric authentication. This process can include following a link or through an ePackage, accessing the hosted server 302 over a secure connection for initial authentication and then for access to the online collaboration. The enrollment 1104 can further include registering a user for biometric authentication, such as capturing a fingerprint scan and creating a public/private key based on the scan. Additionally, users without a biometric authentication device can access the online collaboration through other means, e.g. user ID and password. Also, such users may have limited access for security reasons, e.g. only to post documents, and no access to other areas of the online collaboration.

Once the users are enrolled, the users can participate 1106 in the online collaboration. As discussed herein, each user is authenticated and communicates to the online collaboration through a secure connection. The online collaboration can include text, video, audio, file attachments, calendars, contact lists, memos, to do lists, schedules, action item lists, announcements, task lists, shared documents, and the like. Each time a user logs into the online collaboration, they can be biometrically authenticated providing certification only authorized users are accessing content. Also, each user can be notified whenever a certain change is made to the online collaboration. Further, participation 1106 can include exchanging of ePackages to the hosted server 302. For example, the ePackage 1000 of FIG. 9 can further include a collaboration component.

Figure 12:
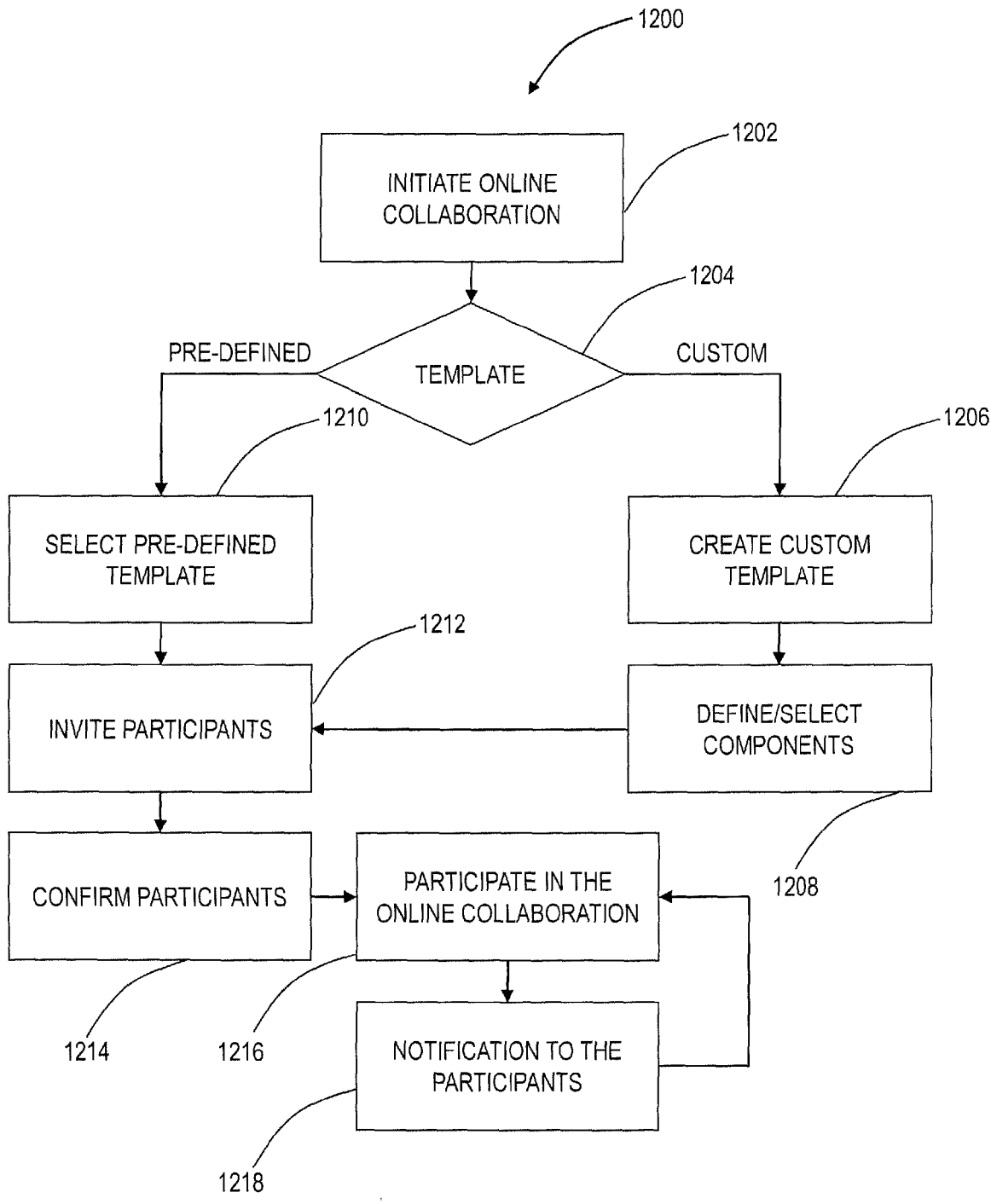
FIG. 12 is a flowchart of an online collaboration according to an exemplary embodiment of the present invention.

Referring to FIG. 12, a flowchart illustrates an online collaboration 1200 according to an exemplary embodiment of the present invention. The online collaboration 1200 is initiated (step 1202). The online collaboration 1200 can be initiated by an authenticated user of the hosted server. This initiation can be through an ePackage. The authenticated user can select a type of template (step 1204), i.e. either an existing pre-defined template or a new, custom template. The template includes a basis for the online collaboration, i.e. appropriate fields, data, etc. If a custom template is selected, the user can create the custom template (step 1206). This is accomplished through defining or selecting components for the template (step 1208). As described herein, components of the template can include, but not limited to, text, video, audio, file attachments, calendars, contact lists, memos, to do lists, schedules, action item lists, announcements, task lists, shared documents, and the like. If a pre-defined template is utilized, the user can select the pre-defined template from a list (step 1210). Templates can include anything from a database structure allowing files to be added, viewed, modified, etc. to a simple template such as solely for a video conference or web conference.

Once the template is selected, the participants are invited (step 1212). The participants can be invited in any manner such as email, voice mail, text message, web posting, instant message, physical notification, etc. The invitation provides details on how the participants should log into the online participation, i.e. hosted server address and details concerning biometric authentication. Each of the participants is excepted to log in to the server and confirm their participation (step 1214). This confirmation can include registering a fingerprint or simply logging in with limited privileges using solely a login ID. The participants then actually participate in the online collaboration (step 1216). The online collaboration 1200 can be anything from a single web conference to a detailed, multi-year project. One feature can include notifying one or more of the participants responsive to certain activity in the online collaboration (step 1218). This can include modified files, new messages/announcements, new members, etc. Note, each time the participants log into the server, the participants provide biometric authentication and work with the server through a secure connection (e.g. HTTPS).

Figure 13:
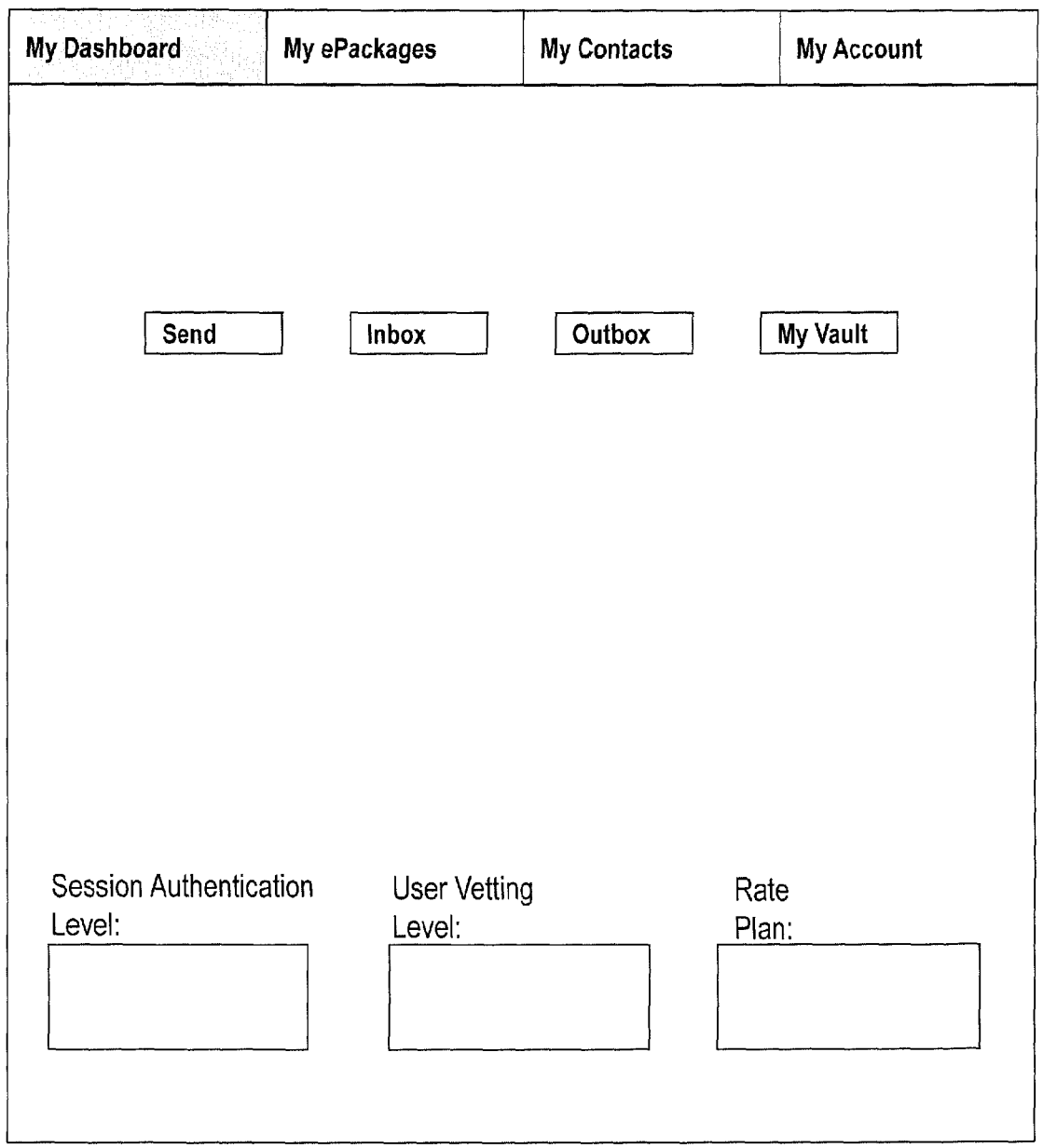

Referring to FIGS. 13-16, various screenshots are illustrated related to online collaboration and ePackages according to exemplary embodiments of the present invention. These screenshots can be displayed on a computer display or the like for a user to interact with the various systems and methods described herein. FIG. 13 illustrates a dashboard that can provide a centralized graphical user interface (GUI) for users to send/receive ePackages and to participate in online collaborations. For example, the dashboard can display a session authentication level, e.g. fingerprint level authentication, user ID/password only authentication, other form of biometric authentication, etc. The dashboard can further display a user vetting level, i.e. showing how the user is registered with the system, and a rate plan for the user. From the dashboard, the user can send ePackages/collaboration requests, view inbox and outbox, and enter a vault. As described herein, the vault can include all of the online collaborations associated with the user.

Figure 14:
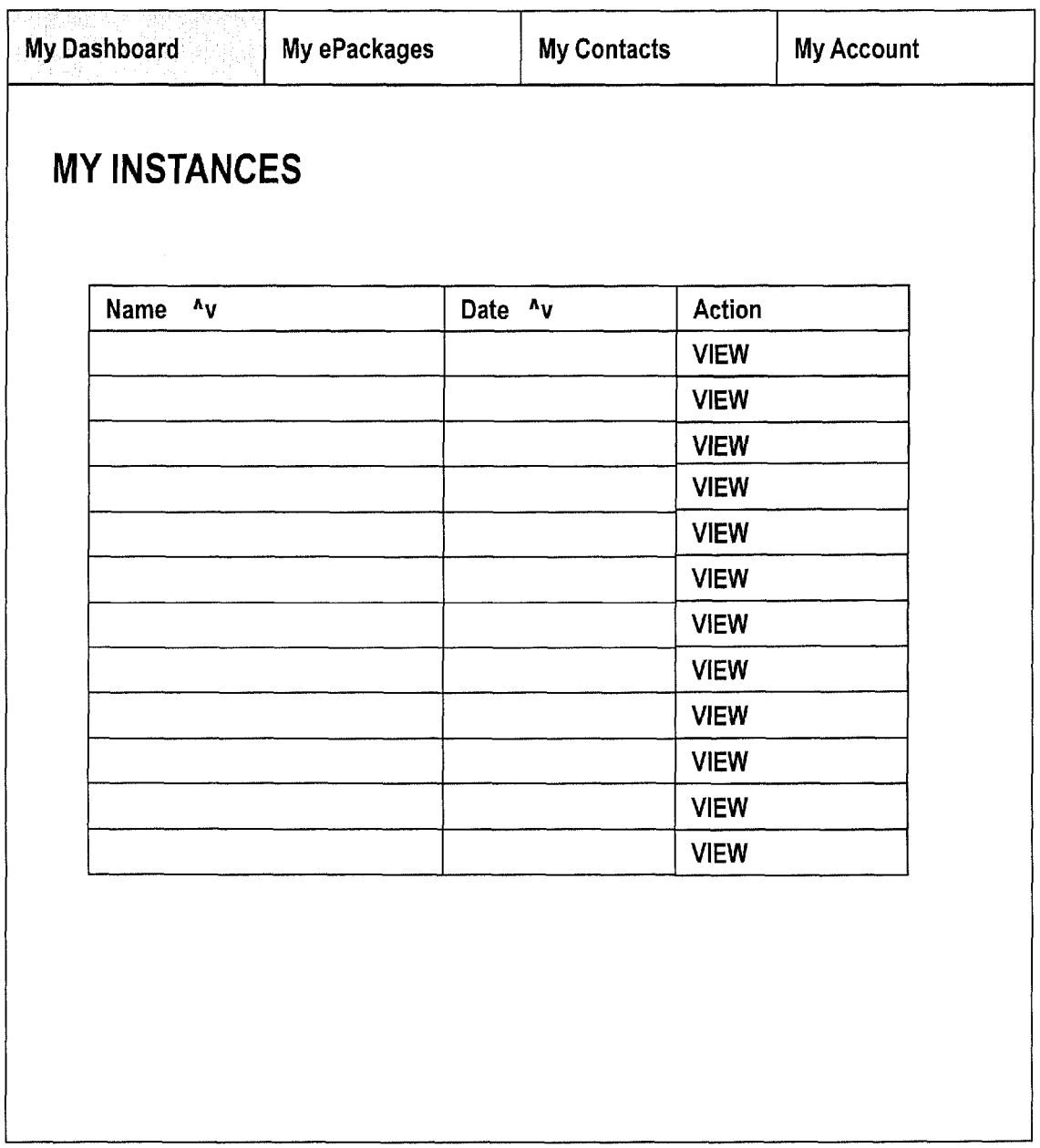

FIG. 14 illustrates a listing of instances in the vault where each instance represents an online collaboration for the user. From the list, the user can view each online collaboration by name and date, and enter each collaboration through a VIEW button. FIG. 15 illustrates a send ePackage GUI. The ePackage GUI can include four tabs, 1. Message, 2. Recipients, 3. Attach Files, and 4. Instances. The Message tab can include text, video, and/or audio for the ePackage. The Attach Files tab can allow the user to attach a plurality of files to the ePackage. The Instances tab can be one or more online collaborations associated with the ePackage. For example, the ePackage can serve as an invitation to join one or more online collaborations. FIG. 15 illustrates the Recipients tab. Here, the user can list each recipient of the ePackage (note, there can be more than one recipient of the same ePackage). Each recipient can include a name, email address, SMS text message address, and there can be associated choices for whether or not a text alert is issued, whether an electronic signature is required, an access code, and whether the recipient is required to provide fingerprint authentication. FIG. 16 illustrates a display of an exemplary ePackage. The ePackage can include a date, a to/from address, a subject, and a message with notes, video, audio, and various shared documents.

Figure 17:
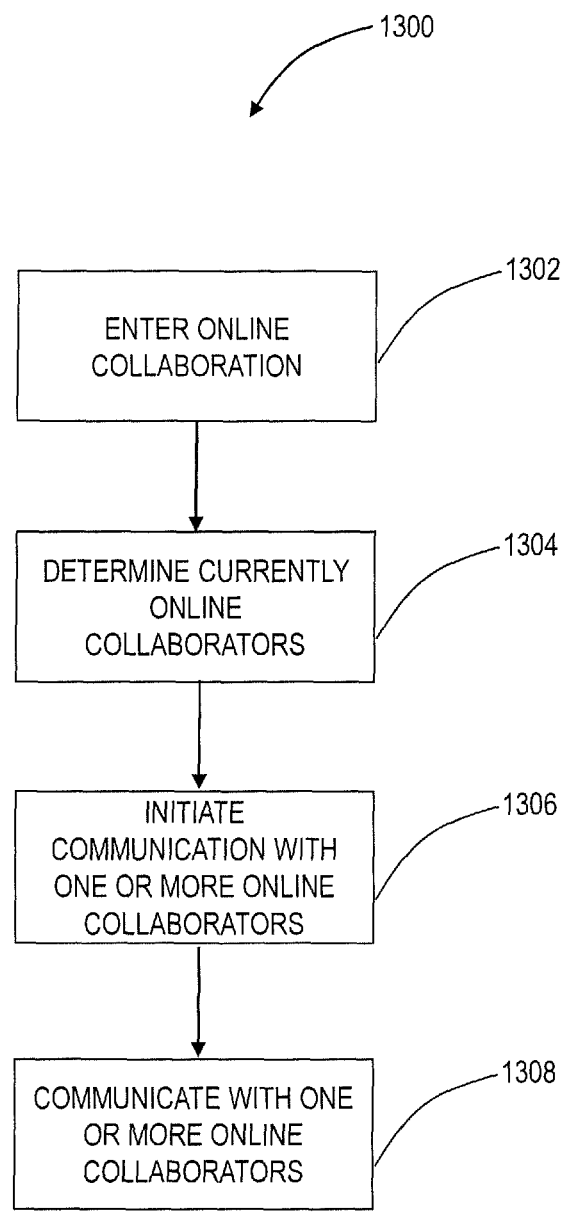
FIG. 17 is a flowchart of a communication method associated with an online collaboration according to an exemplary embodiment of the present invention.

Referring to FIG. 17, a flowchart illustrates a communication method 1300 associated with online collaboration according to an exemplary embodiment of the present invention. This method 1300 can be used in conjunction with the various online collaboration systems and methods described herein. Specifically, a user enters an online collaboration (step 1302) based on the descriptions herein. The user can determine any other collaborators currently online and/or working in the online collaboration (step 1304). For example, there can be a button, link, etc. in the online collaboration GUI to show other users. The user can initiate communication with one or more of the online collaborators (step 1306). Here, the user can send a link, alert, message, etc. requesting communication in the form of chat, video chat, group chat, voice chat, etc. Once one or more of the collaborators accept the request, the users can communicate (step 1308).

In various exemplary embodiments, the systems and methods described herein may further be utilized to provide secure, authentic, verifiable cross domain collaboration electronically over the Internet or other network. Specifically, the present invention may include cross domain collaboration systems and methods that enables collaborative information sharing electronically between a plurality of users from differing domains (i.e. organizations, companies, government agencies) in real-time. Such systems and methods may implement the general structure provided by paper-based and manual security systems in electronic formats thereby removing layers of manual input and increasing collaboration speed. Exemplary applications may include government collaboration (e.g. FBI-NSA-CIA-DOD-DOJ-local law enforcement), industry (e.g. a war room between company executives, financial professionals, outside counsel, etc.), and any other cross domain organizational communications. For example, the U.S. Department of Defense (DOD) has a need for electronic cross domain communications (see, iase.disa.mil/cds/index.html).

The cross domain collaborative systems and methods of the present invention utilize the systems and methods described herein with respect to FIGS. 1-17. Additionally, the cross domain collaborative systems and methods include a plurality of rule sets related to collaborative data. The plurality of rule sets defines access to the collaborative data for each and every user accessing the cross domain collaborative system. In particular, the plurality of rule sets provides various layers of security and may be defined at various points. For example, a first rule set may be defined when a collaborative template is created, a second rule set may be defined upon enrollment of each individual with the collaborative system, and finally, a third rule set may be defined upon inviting an individual to participate in a particular collaboration. In addition, the present invention includes security across all levels of the cross domain collaboration system ensuring each individual accessing the system is authentic and verified, that all information is transmitted with strong encryption, and all information is stored in an encrypted fashion in a physically secure data storage facility.

Figure 18:
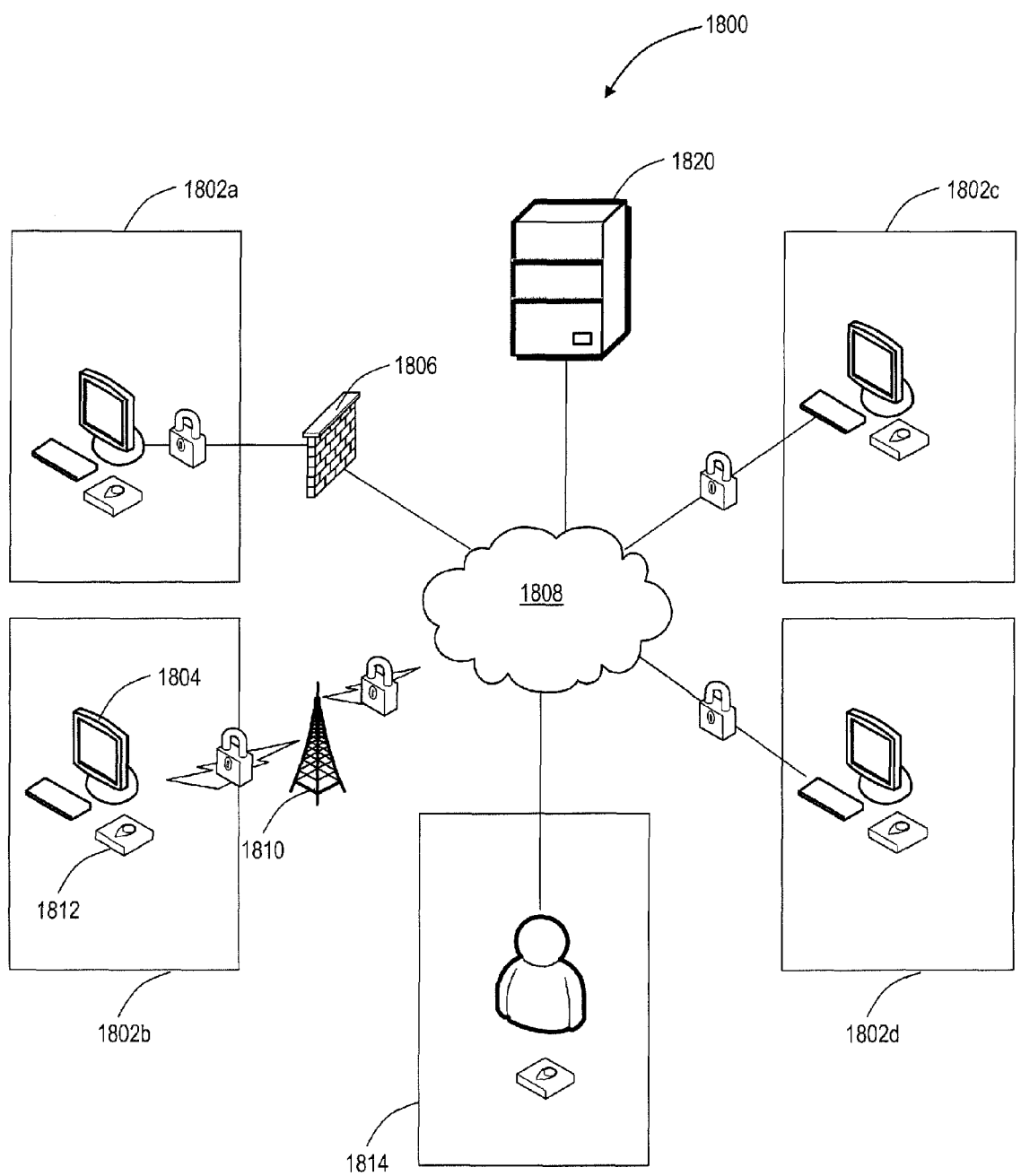
FIG. 18 is a network diagram of a cross domain collaboration system according to an exemplary embodiment of the present invention.

Referring to FIG. 18, in an exemplary embodiment, a network diagram illustrates a cross domain collaboration system 1800. The cross domain collaboration system 1800 may utilize the various systems and methods previously described herein. In general, the cross domain collaboration system 1800 includes a plurality of domains 1802a-1802d each with a plurality of users 1804. Each domain 1802 represents an organization, company, governmental agency, etc. and the user 1804 may include members of the respective domains 1802. The domain 1802 may include secure networks, etc. and may include a firewall 1806 (as shown in the domain 1802a) for security in access a global network 1808, such as the Internet. Also, the domain 1802b may include wireless access 1810 to the global network 1808. As discussed herein, security, authentication, verification, etc. is typically confined to within the individual domains 1802, and there is a need to provide the security authentication, verification, etc. for cross domain collaboration. As described herein, each of the users 1804 across all of the domains 1802 may include an authentication device 1812. This device 1812 may include a fingerprint scanner, a retinal scanner, a DNA device, or other form of biometric security. The device 1812 may be used to authenticate and/or verify each of the users 1804. Specially, the present invention may include a physical registration process 1814 whereby each of the users 1804 is registered in-person providing biometric credentials. Here, each of the users 1804 may be assigned an account with a corresponding access/security level based on a variety of factors, such as the domain membership, individual authorization, etc. Later, the users 1804 may use this account and the corresponding biometric authentication through the device 1812 to participate in the cross domain collaboration system 1800.

The present invention includes a collaboration server 1820 (similar to the hosted server 302) that is also connected to the global network 1808. The collaboration sever 1820 may be physically located within one of the domains 1802 with access to the global network 1808. Further, the collaboration server 1820 is connected to the physical registration process 1814 or the physical registration process 1814 may be implemented at the collaboration server 1820. Specifically, the physical registration process 1814 is configured to preload biometric credentials of all of the users 1804 into the collaboration server 1820 for future access. The collaboration server 1820 operates in a similar manner as described herein with respect to the hosted server 302, i.e. all physical links between the users 1804 and the collaboration server 1820 are encrypted, the collaboration server 1820 stores data in an encrypted format, and the collaboration server 1820 is configured to verify and authenticate all of the accessing users 1804. Additionally, the collaboration server 1820 includes a plurality of rules for creating and populating data in cross domain templates.

Figure 19:
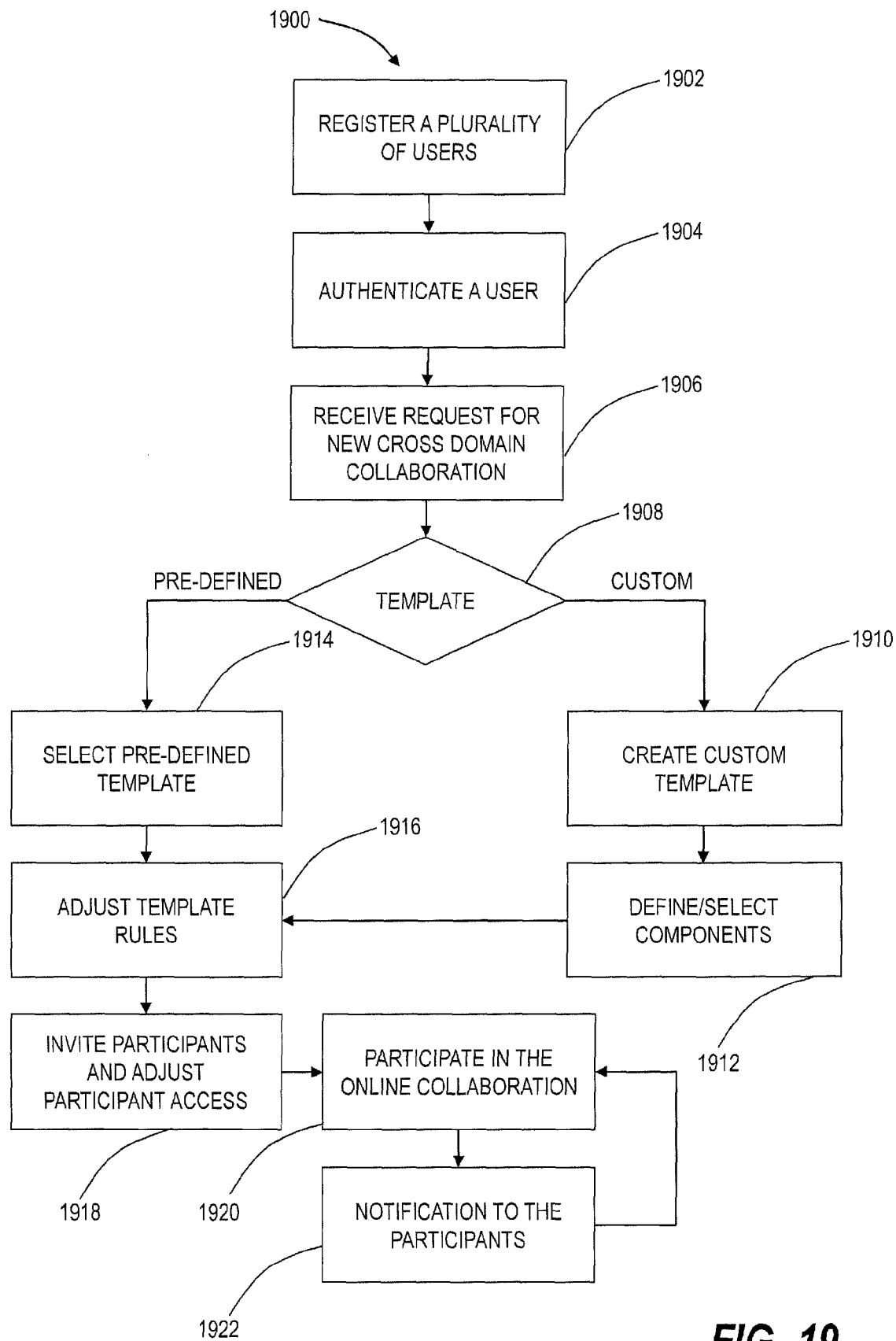
FIG. 19 is a flowchart of a cross domain collaboration method according to an exemplary embodiment of the present invention.

Referring to FIG. 19, in an exemplary embodiment, a flowchart illustrates a cross domain collaboration method 1900 of the present invention. The cross domain collaboration method 1900 may be implemented using the cross domain collaboration system 1800 and the like. The cross domain collaboration method 1900 starts with registering a plurality of users (step 1902). Here, users are provide an account and associated credentials are verified for the users, i.e. biometric credentials. Also, an access level or security level is defined for each of the users. One of the plurality of users may seek access to the cross domain collaboration system, and that user is authenticated (step 1904). Authentication may require a user ID, password, and the like along with the biometric credentials. This user now requests a new cross domain collaboration (step 1906). This may be done through the collaboration server and an associated graphical user interface (GUI). The new cross domain collaboration may be initiated through a custom template or a pre-defined template (step 1908). As described herein, the templates provide a format and view of the cross domain collaboration. The templates include formats for presenting the information associated with the cross domain collaboration. For example, the templates may be in a wiki format.

If a custom template is selected, the user may create a custom template (step 1910). Here the user may name the template and save it for future use. Additionally, the template may be accessible to any of the users for future use. The user then defines and/or selects associated components of the template (step 1912). Here, the system provides the user the ability to create different formats, i.e. placing of information, notes, files, calendars, etc. If a pre-defined template is selected, the user selects the desired template from a list (step 1914). Note, the list may include various templates including previously created custom templates. For example, the present invention may be used in situational awareness for threats. Each new situation may utilize the same template. At this stage, the user creating the new cross domain collaboration may adjust rules associated with template components (step 1916).

The present invention includes multiple levels of rules handling data in a cross domain collaboration. Rules define who may view, edit, forward, etc. data in the collaboration. For example, in the situational awareness scenario, the domains may include the FBI, the DOD, the NSA, local law enforcement, and private industry. There may be requirements to share some, but not all of the information in the situational awareness. For example, high level officials in the government may be able to view all of the situational awareness, but the private industry may only be needed to see low-level or unclassified information. Assume an exemplary situational awareness scenario includes a threat against utility networks and infrastructure. This may require a cross domain collaboration between various governmental agencies and private utility workers. All information may be desired to be shared to those government officials with top secret clearance. However, there is a need to have people in the field involved in the collaboration, e.g. utility employees. For example, the situational awareness may be a cyber threat against utilities. Here, there may be a variety of information from top secret (e.g. identifying sources of the threats, possible outcomes, etc.) to low level unclassified information (e.g. statement concerning possible network issues at utility companies). A private utility collaborator may realize their Internet connectivity is problematic, and post such a description on the cross domain collaboration.

After setting the template and the associated rules, the user may invite participants and also adjust rules for individual participants (step 1918). Note, each of the participants is (or becomes through the registration process) a registered user. Accordingly, each user has an associated security level, rating, etc. When being invited, the user setting up the cross domain collaboration may decide to alter individual participants' access ability. This may include managing security access in a downward fashion. For example, assume the user setting up the collaboration has a secret clearance. The user may adjust other users to lower than secret clearances, but may not adjust higher—i.e. providing someone with a secret clearance top secret access (cannot give more access, but may give less). Accordingly, the present invention includes three different times when rules are settable for the cross domain collaboration—1) during registration of individual users; 2) during template creation; and 3) during individual participant invitation. Also, invitation to the cross domain collaboration may be via an ePackage as described herein. Finally, the users may participate in the cross domain collaboration (step 1920), and each time information is updated or changed in the template, each user may receive a notification (e.g. email, etc.) (step 1922).

Figure 20:
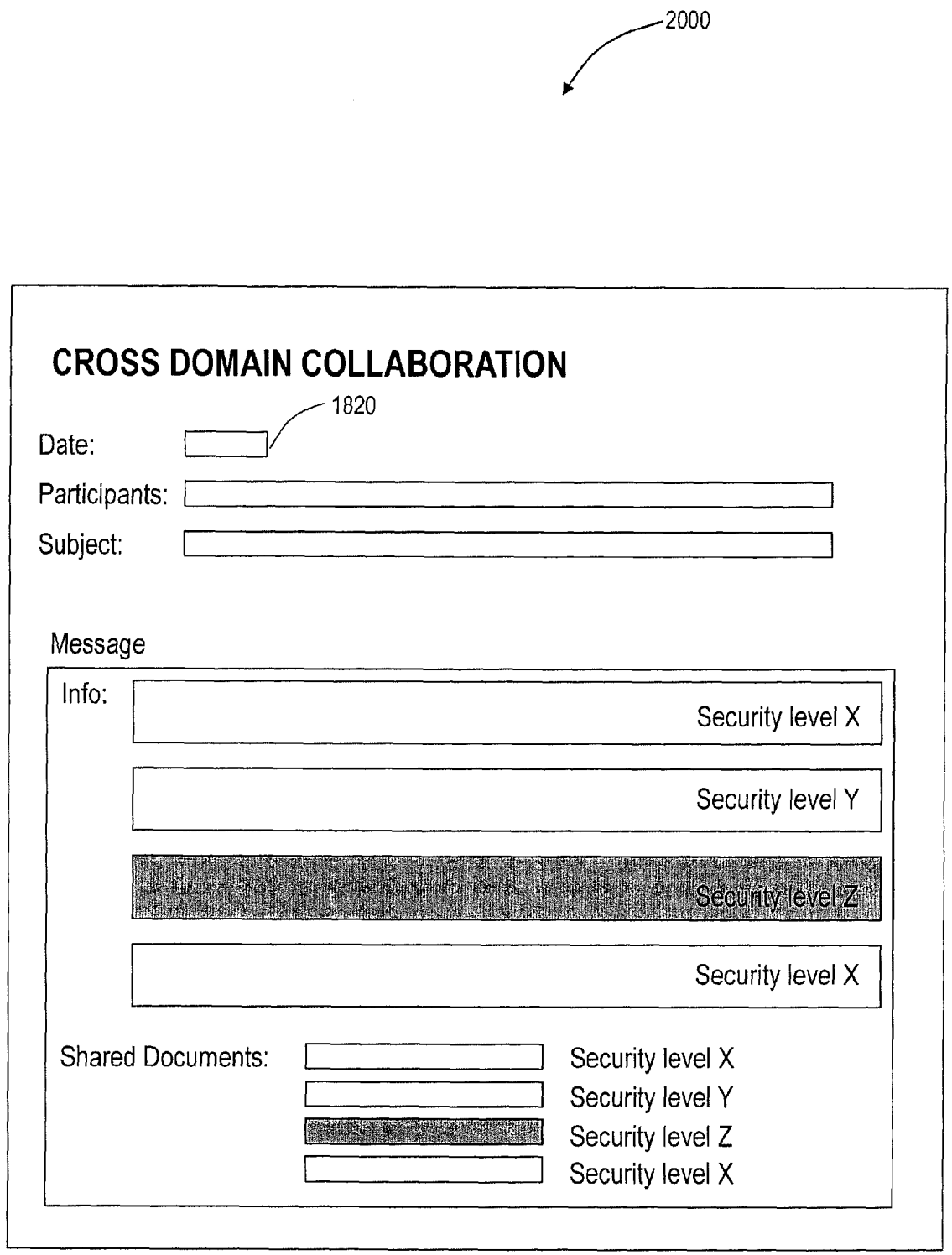
FIG. 20 is a screen shot of an exemplary cross domain collaboration according to an exemplary embodiment of the present invention.

Referring to FIG. 20, in an exemplary embodiment, a screen shot illustrates an exemplary cross domain collaboration 2000. The cross domain collaboration 2000 can be displayed on a computer display or the like for a user to interact with the various systems and methods described herein. The principal purpose of the cross domain collaboration 2000 is to share information. All or some of the information posted to the cross domain collaboration 2000 may include a security level, rating, etc. As described above, every user of the cross domain collaboration 2000 has a certain level, rating, etc., and this is used to determine whether or not a particular user may view the information. For example, assume the user of the cross domain collaboration 2000 is rated at a security level Y and X. Here, the information above this rating, i.e. security level Z, may be blacked out or simply unavailable for viewing. Note, the user may post information, but only information at the security levels Y and X. Information that is posted to the cross domain collaboration 2000 may be tagged with an appropriate security level by the user posting the information. Additionally, the cross domain collaboration 2000 may use code word classification whereby the cross domain collaboration 2000 automatically tags an appropriately security level to all posted information based on an analysis of the content, keywords, etc. Alternatively, the information posted may be automatically tagged at the security level of the user posting the information.

The present invention takes groups of users and groups of documents and couples them therebetween. Conventionally, there is a one-to-one correspondence between a user and a document. That is, a user is granted permission for access to each document, and this permission is typically tied back to the user's password for access. The present invention uses the user's password for authentication/access to the system, and further uses a user's classification level to determine access to a group of documents. That is, access to documents is not based on users, but rather on classification level. For example, a document may be created or uploaded at a particular classification level and all of the authorized users obtain their access to the document based on this level.

Figure 21:
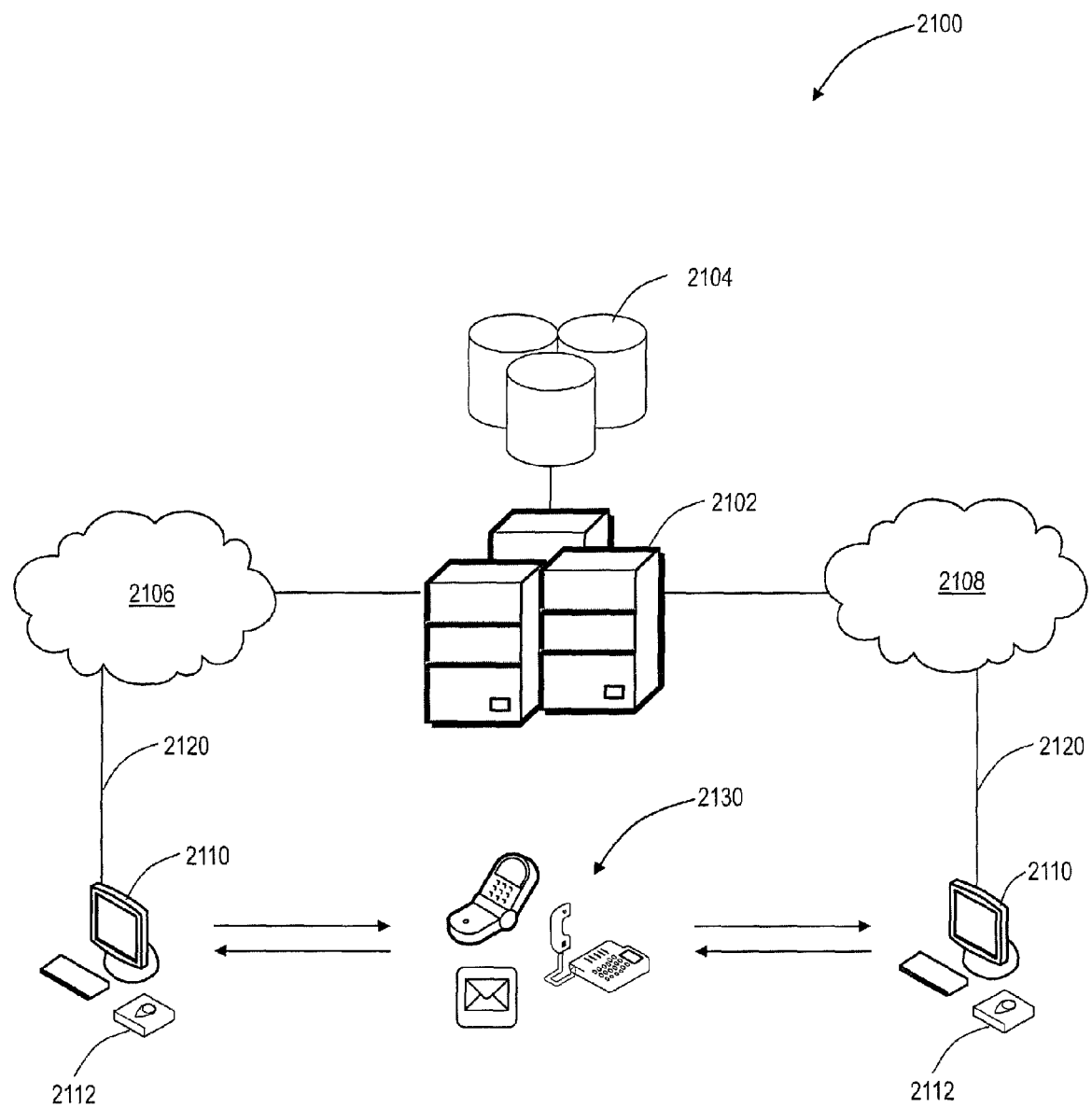
FIG. 21 is a network diagram of a certified, secure, and authentic electronic messaging and collaboration system according to an exemplary embodiment of the present invention.

Referring to FIG. 21, in an exemplary embodiment, a certified, secure, and authentic electronic messaging and collaboration system 2100 is illustrated. The system 2100 includes one or more servers 2102 optionally connected to data storage 2104. The servers 2102 are connected to networks 2106, 2108 which may both include the Internet, a virtual private network (VPN), a local area network (LAN), a wireless network (including all types), and the like. As described herein, the servers 2102 are configured to enable a plurality of users 2110 to electronically communicate in a secure, certified, and authenticated manner through the servers 2102. Each of the users 2110 may be authenticated through a biometric device 2112 that may be configured to implement the various processed described herein (e.g., FIG. 7). In an exemplary embodiment, each of the users 2110 communicates through the networks 2106, 2108 via an encrypted link 2120 that may include any of Advanced Encryption Standard (AES), Server Gated Cryptography (SGC), Federal Information Processing Standard (FIPS) Publication 140-2 from the National Institute of Standards and Technology (NIST), and the like. In an exemplary embodiment, the link 2120 may include Extended Validation Secure Sockets Layer (SSL) SGC Certificate Authorities (CA) (e.g., VeriSign CA). With SGC (Server Gated Cryptography) a hacker with the time, tools, and motivation to attack using brute force would require a trillion years to break into a session protected by a SGC-enabled certificate. The link 2120 may further include AES-256 which enables 256-bit encryption, and is much stronger than 128-bit (note, this requires the user's 2110 browser to supports 256-bit encryption). Also, the link 2120 may include NIST/FIPS 140-2 CVMP (Validation certificate available). For users connecting with older browsers, the system 2100 may utilize 128-bit encryption. Certain older browsers and operating systems still cannot may not be able connect at this level, and users 2110 with the following browser versions and operating systems will temporarily step-up to 128-bit SSL encryption (1) Internet Explorer export browser versions from 3.02 but before version 5.5; (2) Netscape export browser versions after 4.02 and up through 4.72; and (3) Windows 2000 systems shipped prior to March 2001 that have not downloaded Microsoft's High Encryption Pack or Service Pack 2 and that use Internet Explorer.

In addition to this transmission encryption, the servers 2102 and the data storage 2104 may also include data encryption on stored data utilizing any of AES, AES-256, FIPS Publication 140-2, and the like. For Storage Protection, the data center housing the servers 2102 may be Statement on Auditing Standards No. 70 (SAS 70) type 2 compliant with Distributed Denial Of Service attack (DDoS) protection, the firewall 2202, and the servers 2102 may include a hardened operating system. The servers 2102 and the data storage 2104 may provide data encryption on the stored data. For example, this may include SQL server 08 with Transparent Data Encryption to enable encryption of an entire database, data files, or log files, without the need for application changes. Benefits of this include: Search encrypted data using both range and fuzzy searches, search secure data from unauthorized users, and data encryption without any required changes in existing applications. Additionally, each ePackage, collaboration, etc. may include AES-256 encryption. This may include the Microsoft Cryptographic Application Programming Interface (CryptoAPI) which is part of the Win32 API, the CryptoAPI architecture is somewhat similar to Open Database Connectivity (ODBC) in that it includes an API layer (analogous to ODBC Manager) and a number of cryptographic modules underneath that layer that actually perform cryptographic tasks (analogous to ODBC drivers), and the NIST/FIPS 140-2 CVMP (Validation certificate available). Further, the system 2100 may further include a secondary communication mechanism 2130 between any of the users 2110. The secondary communication mechanism 2130 may include any of email, text messaging, Interactive Voice Response (IVR), and the like. The mechanism 2130 may be utilized to inform any of the users 2110 of an ePackage, an update to a collaboration, or the like. Of note, the mechanism 2130 is not meant to convey data but rather to convey that data has been updated or new data is available on the servers 2102.

Figure 22:
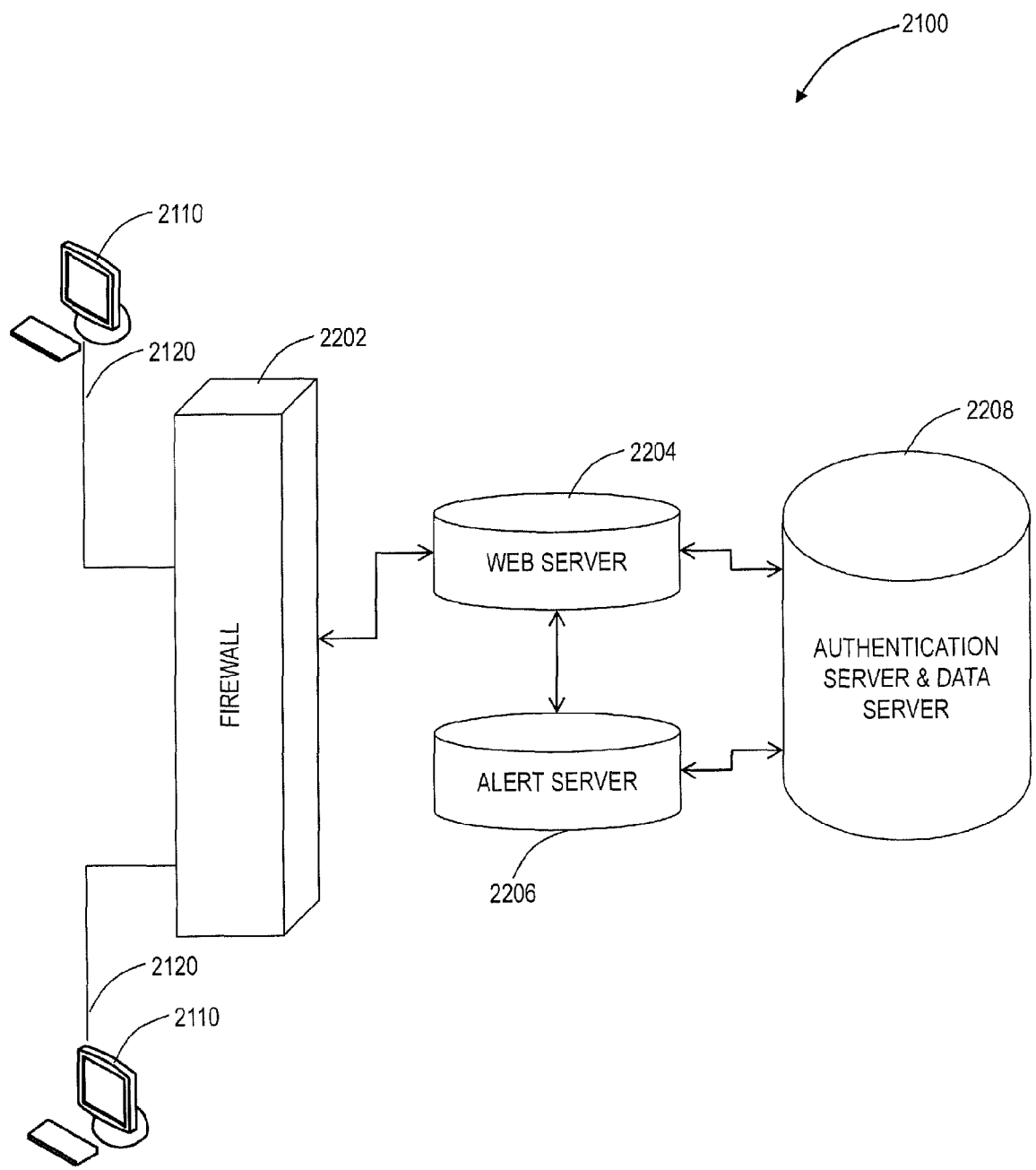
FIG. 22 is a block diagram of the functionality of one or more servers illustrated in FIG. 21 according to an exemplary embodiment of the present invention.

Referring to FIG. 22, in an exemplary embodiment, a block diagram illustrates functionality of the one or more servers 2102. In this exemplary embodiment, the servers 2102 include a firewall 2202, a web server 2204, an alert server 2206, and an authentication and data server 2208. Those of ordinary skill in the art will recognize this as an exemplary configuration and realize that there may be more or less servers to perform more or less functionality. The firewall 2202 is configured to prevent intrusions from the networks 2106, 2108 to the servers 2102, and in an exemplary embodiment, the firewall 2202 may include a Managed Firewall Cisco ASA 5510SP (available from Cisco Systems). The web server 2204 communicates to the users 2110 through the firewall 2202 via the links 2120. The web server 2204 further directs the communications from the users 2110 between the alert server 2206 and the authentication and data server 2208. The alert server 2206 is configured to manage alerts related to new and existing ePackages, collaborations, etc. This includes tracking, notification, delivery recall, and the like. The authentication and data server 2208 provides both authentication of the users 2110 as well as data storage of the ePackages, collaborations, etc. In an exemplary embodiment, the servers 2204, 2206, 2208 may include Dell PowerEdge Server (or equivalent) (available from Dell) operating a variant of Windows Server (available from Microsoft).

Figure 23:
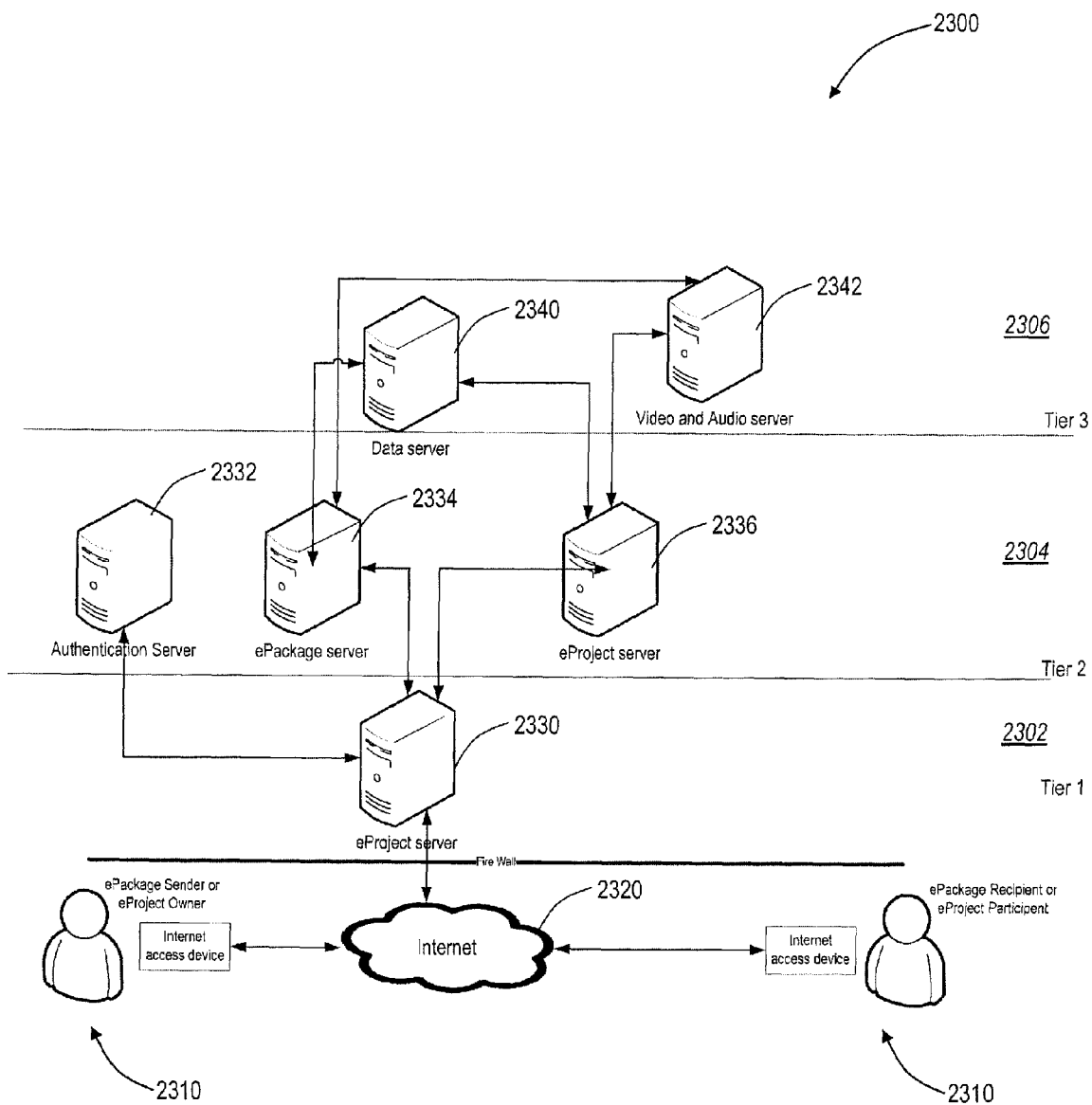
FIG. 23 is a block diagram of a network system utilized in the various exemplary embodiments described herein.

Referring to FIG. 23, in an exemplary embodiment, a block diagram illustrates a network system 2300 utilized in the various exemplary embodiments described herein. The network system 2300 includes a data center with three tiers 2302, 2304, 2306 providing access and hosting of ePackages, eProjects, and the like. Users 2310 may exchange ePackages, collaborate on eProjects, and the like via a network, such as the Internet 2320 and the data center. For security purposes, only the first tier 2302 is connected to the Internet 2320. Furthermore, user data is only in the third tier 2306 which is another tier removed from the Internet. Specifically, the first tier 2302 may include an eProject server 2330 which is communicatively coupled to the users 2310 via the Internet 2320. The eProject server 2330 may be configured to provide a User Interface to the users 2310 and to allow them to interact with the various embodiments described herein. The second tier 2304 may include an authentication server 2332, an ePackage server 2334, and an eProject server 2336, each of which is communicatively coupled to the eProject server 2330. The authentication server 2332 is configured to store data related to the users 2310 for secure authentication, such as described herein in FIGS. 7a-7c. The ePackage server 2334 is configured to create, modify, etc. ePackages between the various users 2310. The eProject server 2336 is configured to create, modify, etc. eProjects collaborated on by the various users 2310. The third tier 2306 includes a data server 2340 and a video and audio server 2342 that are each communicatively coupled to the ePackage server 2334 and the eProject server 2336. Of note, the servers 2340, 2342 contain secure, confidential user data in the form of ePackages, eProjects, and the like and these are only connected to the Internet 2320 via the tiers 2302, 2304 providing an extra layer of security.

Figure 24:
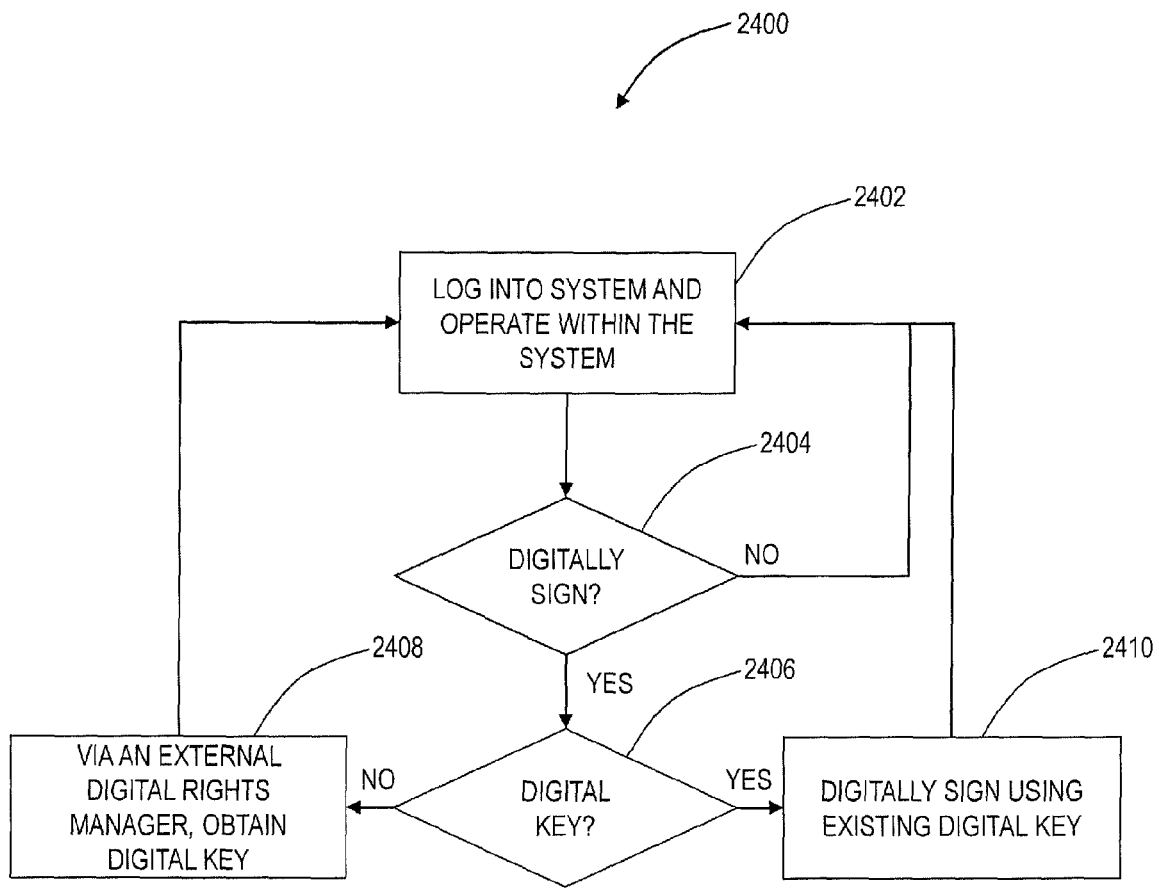
FIG. 24 is a flowchart of method for digitally signing files, emails, etc. in an ePackage.

Referring to FIG. 24, in an exemplary embodiment, a method 2400 illustrates a process for digitally signing files, emails, etc. in an ePackage 1000. Conventionally, authenticated signatures require a recipient of the ePackage 1000 to print out the file, manually sign printed papers, and scanning the signed printed papers. Obviously such a conventional process is inefficient when viewed in context of the systems and methods described herein. Other convention mechanisms include using a so-called electronic signature, using text characters such as /s/, etc. However, these mechanisms do not provide verification of the actual signature or may be hacked via software tools. The method 2400 provides a secured, verified process for digitally signing documents, files, emails, etc. within the systems and methods of the present invention. The method 2400 is configured to operate while a user is logged in or following the user logging into the servers 300, 302 (step 2402), and the method 2400 may be used anytime the user wishes to digitally or electronically sign a document, email, file, ePackage, etc. (step 2404).

The method 2400 utilizes a digital key (step 2406), and if the user does not have a digital key, the method 2400 enables the user to obtain such a key via an external digital rights manager (step 2408). Here, the user may be redirected while being logged into the server 300, 302 to an external provider, e.g. using secure SSL links, to register and obtain the digital key. The external provider is configured to authenticate the user and provide a digital key along with an associated password to the user. In an exemplary embodiment, the password may require biometric authentication along with entry of the password. In another exemplary embodiment, the password may simply include the biometric authentication. Note, the digital key may be maintained locally at the servers 300, 302 and not with the user's machine. If the user has a digital key (step 2406), then the user may sign any document, file, etc. using the digital key (step 2410). In an exemplary embodiment, the systems and methods described herein may include a GUI button to digitally sign any document, file, etc. used in the system.

Referring to FIG. 25, in an exemplary embodiment, a screen shot illustrates viewing management for files in an exemplary ePackage. Specifically, for security and confidentiality, the present invention contemplates rules that may be enforced on files, text, documents, etc. associated with an ePackage (or on the entire ePackage). These rules are enforced by the system and limit a recipients ability to perform various tasks with the files. For example, the rules may include a full permission whereby the recipient can do anything with the files, i.e. read, save, forward, print, view, etc. Also, the rules may include a reply/forward prevention rule whereby the recipient is prevented from replying or forwarding the files. The rules may also include a view/read only whereby the recipient is only able to view the files on through the servers 300, 302, i.e. the recipient is prevented from saving a local copy. The rules may also include a print allowed rule determinative of whether the recipient can print the files. Additionally, the rules may include a screen capture prevention rule where the servers 300, 302 are configured to prevent the recipient from using locally installed print screen functionality (e.g., CTRL-ALT-PRINT SCREEN in Windows, the Sniping Tool in Windows 7, etc.). Finally, the rules may include a screen mask to prevent external devices (e.g. camera phones, etc.) from taking pictures of a screen with the files being viewed. This may be accomplished by requiring the recipient to view the files using the cursor to selectively show a portion of text at a time. Alternatively, this may be accomplished via watermarking on the screen. Note, the present invention contemplates use of one or more rules in conjunction with each other.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. A cross domain collaboration system, comprising:
a server comprising a network interface connected to the Internet, a data store comprising electronic data storage, and a processor, wherein each of the network interface, the data store and the processor are communicatively coupled, and wherein the network interface, the data store and the processor are collectively configured to:
remotely biometrically authenticate a plurality of users, wherein each of the plurality of users comprises a security level and a domain; and
enable cross domain collaboration between the plurality of users based on the security level of each of the plurality of users;

wherein to biometrically authenticate a user of the plurality of users, the network interface, the data store and the processor are collectively configured to:
send software code to a device associated with the user;
obtain a biometric identification of the user at the device;
create a numerical index of the obtained biometric identification to form a public key at the device;
receive the public key from the device; and
authenticate the public key with a corresponding private key in an authentication database.

2. The cross domain collaboration system of claim 1, wherein each of the plurality of users communicates to the server through a secure connection over the Internet, wherein the secure connection over the Internet comprises a Hypertext Transfer Protocol Secure (HTTPS) connection, and wherein the secure connection traverses outside at least one domain of the plurality of users.

3. The cross domain collaboration system of claim 1, wherein the network interface, the data store and the processor are collectively further configured to:
enable one of the users to set up the cross domain collaboration and invite participants comprising the plurality of users; and
adjust the security level of one or more of the plurality of users, wherein the security level is adjusted downward only.

4. The cross domain collaboration system of claim 1, wherein the network interface, the data store and the processor are collectively further configured to:
register the user for biometric authentication, wherein to register comprises capturing a fingerprint scan of the user and storing the private key in the authentication database responsive to the fingerprint scan; and
set the security level of the user.

5. The cross domain collaboration system of claim 1, wherein the cross domain collaboration comprises a sharing of files comprising any of text, video, audio, file attachments, calendars, contact lists, memos, to do lists, schedules, action item lists, announcements, and task lists between the plurality of users.

6. The cross domain collaboration system of claim 5, wherein the files are stored in the data store and encrypted with one of Triple Data Encryption Standard (T-DES) and Advanced Encryption Standard (AES) encryption.

7. The cross domain collaboration system of claim 1, wherein the data store comprises a plurality of templates for the cross domain collaboration.

8. The cross domain collaboration system of claim 7, wherein the network interface, the data store and the processor are collectively further configured to:
create a new template and store the created template among the plurality of templates; and
adjust security associated with one of the plurality of templates.

9. The cross domain collaboration system of claim 1, wherein the network interface, the data store and the processor are collectively further configured to:
tag all information posted to the cross domain collaboration with a certain security level; and
restrict viewing of the information among the plurality of users based on the certain security level associated with the information.

10. The cross domain collaboration system of claim 1, wherein the network interface, the data store and the processor are collectively further configured to:
code word classify information in the cross domain collaboration responsive to an analysis of the information.

11. Across domain collaboration method, comprising:
receiving a selection of a template from a plurality of templates for a cross domain collaboration;
adjusting security associated with the selected template;
receiving a list of a plurality of users for the cross domain collaboration;
adjusting security associated with each of the plurality of users;
biometrically authenticating each of the plurality of users prior to participation in the cross domain collaboration; and
displaying information in the cross domain collaboration based on a security level of each user;
wherein the biometrically authenticating comprises:
sending software code to a device associated with a user of the plurality of users;
obtaining a biometric identification of the user at the device;
creating a numerical index of the obtained biometric identification to form a public key at the device;
receiving the public key from the device; and
authenticating the public key with a corresponding private key in an authentication database.

12. The cross domain collaboration method of claim 11, further comprising:
creating a custom template for the cross domain collaboration.

13. The cross domain collaboration method of claim 11, wherein the template comprises a collection of any of text, video, audio, file attachments, calendars, contact lists, memos, to do lists, schedules, action item lists, announcements, and task lists.

14. The cross domain collaboration method of claim 11, further comprising:
registering the user for biometric authentication, wherein to register comprises capturing a fingerprint scan of the user and storing the private key in the authentication database responsive to the fingerprint scan; and
setting security for the user.

15. The cross domain collaboration method of claim 11, further comprising:
communicating with each of the plurality of users through a secure connection over the Internet for the cross domain collaboration.

16. The cross domain collaboration method of claim 15, wherein the secure connection over the Internet comprises a Hypertext Transfer Protocol Secure (HTTPS) connection.

17. The cross domain collaboration method of claim 10, wherein files associated with the cross domain collaboration are stored in a secure data store and encrypted with one of Triple Data Encryption Standard (T-DES) and Advanced Encryption Standard (AES) encryption.

18. A secure computer system connected to a plurality of users, comprising:
a cross domain server with a network connection to the Internet;
an authentication database communicatively coupled to the hosted server;
a data store communicatively coupled to the cross domain server, wherein the data store comprises data storage for a cross domain collaboration;
a plurality of users each with a networked device connected to the Internet, wherein the networked device comprises a biometric authentication device and each of the plurality of users comprises a security level;
wherein the cross domain server is configured to host the cross domain collaboration between the plurality of users through a secure Hypertext Transfer Protocol Secure (HTTPS) connection to each of the plurality of users and through biometric authentication of each of the plurality of users prior to accessing the online collaboration, and wherein information is displayed to each of the plurality of users based upon a security level associated with each of the plurality of users; and wherein the biometric authentication of a user of the plurality of users comprises:

sending software code from the cross domain server to the networked device;

obtaining a biometric identification of the user at the networked device;

creating a numerical index of the obtained biometric identification to form a public key at the networked device;

receiving the public key at the cross domain server from the networked device; and authenticating the public key with a corresponding private key in the authentication database.

* * * * *